United States Patent [19]

Shinkai et al.

[11] Patent Number: 5,075,436

[45] Date of Patent: Dec. 24, 1991

[54] CHIRAL 1-β-METHYL-CARBAPENEM INTERMEDIATES

[75] Inventors: Ichiro Shinkai, Westfield; Anthony O. King, Colonia; Lelia M. Fuentes, Westfield, all of N.J.

[73] Assignee: Merck & Co., Inc., Rahway, N.J.

[21] Appl. No.: 300,739

[22] Filed: Jan. 19, 1989

Related U.S. Application Data

[63] Continuation of Ser. No. 157,166, Feb. 11, 1988, abandoned, which is a continuation of Ser. No. 817,184, Jan. 8, 1986, abandoned.

[51] Int. Cl.$^5$ .......................................... C07D 205/08
[52] U.S. Cl. ................................................ 540/200
[58] Field of Search ........................................ 540/200

[56] References Cited

U.S. PATENT DOCUMENTS

| | | | |
|---|---|---|---|
| 4,206,219 | 6/1980 | Christensen et al. | 540/200 |
| 4,234,596 | 11/1980 | Christensen et al. | 540/200 |
| 4,309,346 | 1/1982 | Christensen et al. | 540/200 |
| 4,383,946 | 5/1983 | Christensen et al. | 540/200 |
| 4,427,586 | 1/1984 | Numata et al. | 540/200 |
| 4,521,337 | 6/1985 | Southgate et al. | 540/200 |

FOREIGN PATENT DOCUMENTS 0010317 4/1980 European Pat. Off. .
0067517 12/1982 European Pat. Off. .

OTHER PUBLICATIONS

Sunagawa, Chem. Abs. 106, 4750 (1986).
D. H. Shih et al., Heterocycles, vol. 21, pp. 29–40 (1984).
L. F. Feiser, Reagents for Organic Synthesis, vol. 1, pp. 723–729.
Yanagisawa, Tetrahedron Letters, vol. 23, No. 33, pp. 3379–3382 (1982).
Shonogi, Chem. Abstr. 97:162703m (1982).
Phillips, Tetrahedron Letters, vol. 24, No. 4, pp. 335–338 (1983).
Aoki, Chem. Abstr. 97:23504j (1982).
Prasad, Tetrahedron Letters, vol. 23, No. 12, pp. 1247–1250 (1982).
Greengras, Tetrahedron Letters, vol. 22, pp. 1161–1164 (1981).
Kametani, Heterocycles, vol. 19, No. 6, pp. 1023–1032 (1982).

*Primary Examiner*—Richard L. Raymond
*Attorney, Agent, or Firm*—Raymond M. Speer; Hesna J. Pfeiffer

[57] ABSTRACT

A multistep process is described for selectively obtaining 1-β-methylcarbapenem intermediates in high overall yield. The desired 1-β-methyl chirality is obtained through the hydrogenation of certain bicyclic β-lactam ring structures containing an exocyclic methylene double bond alpha to the β-lactam ring, in the presence of a metallic nickel hydrogenation catalyst. The hydrogenation results in a mixture of α- and β-methyl isomers having a high β/αepimeric molar ratio. New 1-β-methylcarbapenem intermediates containing the exocyclic double bond are also described.

5 Claims, No Drawings

CHIRAL 1-β-METHYL-CARBAPENEM INTERMEDIATES

This is a continuation of application Ser. No. 157,166, filed Feb. 11, 1988, now abandoned, which is a continuation of application Ser. No. 817,184, filed Jan. 8, 1986, now abandoned.

BACKGROUND OF THE INVENTION

This invention relates to a multistep chiral process for selectively obtaining high yields of 1-β-methylcarbapenem intermediates for the subsequent synthesis of 1-β-methylcarbapenem antibiotics. The process involves introducing an exocyclic α-methylene double bond into a bicyclic β-lactam ring structure by means of α-alkylation, followed by α-selenation and then oxidation to form the exocyclic α-olefin, and then reduction to form the amine-alcohol, followed by cyclization to form a bridging-protecting group. The exocyclic double bond is then subjecting the compound to hydrogenation conditions with a metallic nickel hydrogenation catalyst which preferentially results in the formation of the 1-β-methylcarbapenem intermediate.

1-β-Methylcarbapenems, as described in the reference *Heterocycles*, 1984, Vol. 21, pp. 29–40 by D. H. Shih, F. Baker, L. Cama and B. G. Christensen, are extremely useful and effective broad spectrum antibiotics, useful against a wide variety of bacteria including Gram-positive bacteria including *S. aureus, Strep. sp., B. subtilis*, and Gram-negative bacteria such as *E. coli, Shigella sp., Enterobacter sp., Klebsiella sp., Proteus, Serratia* and *Pseudomonas sp.*

A method of synthesizing 1-β-methylcarbapenems is described in the above-cited reference in which the beta-methyl chirality is introduced into the molecule by base-catalyzed alkylation producing a mixture of α and β isomers which are separated by chromatographic procedures.

However, because of the relatively low β/α epimeric ratio obtained by this alkylation route, newer methods for obtaining the desired β-methyl intermediate on a larger scale are constantly being sought.

SUMMARY OF THE INVENTION

It has been found that by introducing an exocyclic α-methylene double bond onto an alkyl ester side chain of a beta-lactam, followed by ester reduction and cyclization to a bicyclic β-lactam ring system, and then subjecting said compound to hydrogenation conditions utilizing a specially treated metallic nickel hydrogenation catalyst, the stereochemistry of the molecule enables the hydrogenation to proceed stereoselectively to produce the β-methyl isomer is a β/α epimer ratio greater than 1 and as high as 15:1.

In accordance with this invention there is provided:
a compound of the structural formula

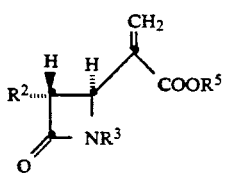

wherein $R^2$ is independently selected from the hydrogen, linear or branched $C_1$–$C_3$ alkyl, which can be substituted with fluoro, hydroxy or protected hydroxy; $R^3$ is H or a protecting group and $R^5$ is H or $C_1$–$C_4$ alkyl.

Further provided is:
a process comprising the steps of:
a) contacting a compound of the structural formula:

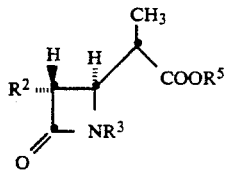

with a selenating agent to form a compound of the structural formula: and,

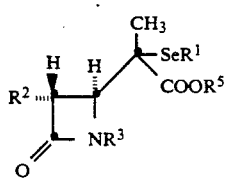

b) contacting said compound resulting from step (a) with an oxidizing agent to form a compound of the structural formula:

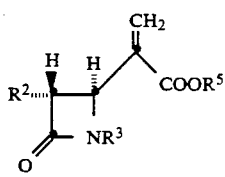

wherein above; $R^1$ is $C_1$–$C_4$ alkyl, $C_6$–$C_{10}$ aryl, or heteroaryl, which can contain substituents inert under the conditions of forming structure IV; $R^2$ is independently selected from hydrogen, linear or branched $C_1$–$C_3$ alkyl, which can be substituted with fluoro, hydroxy or protected hydroxy; $R^3$ is hydrogen or a protecting group; and $R^5$ is hydrogen or $C_1$–$C_4$ alkyl.

Also provided is:
A process comprising the steps of:
a) alpha-methylating a compound of the structural formula:

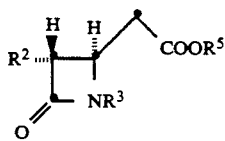

by contacting therewith in the presence of an enolating agent and a methylating agent to yield a compound of the structural formula:

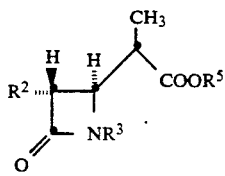

b) contacting said compound resulting from step (a) with a selenating agent to form a compound of the structural formula:

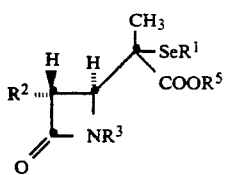

III c) contacting said compound resulting from step (b) with an oxidizing agent to form a compound of the structural formula:

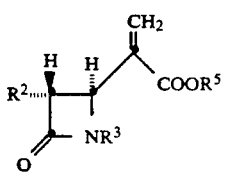

IV d) contacting said compound of structural formula (IV) with an alkyl aluminum hydride reducing agent, in a solvent therefor, to form a compound of the structural formula:

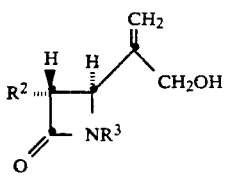

V e) contacting said resulting Compound V with a ketone, aldehyde or organosilicon group to form a compound of the structure:

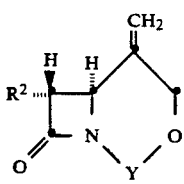

VI wherein Y is a divalent bridging-protecting group, derived from said ketone, aldehyde or organosilicon group, said group being stable to catalytic hydrogenation and removable by acid or base hydrolysis:

f) contacting said Compound VI with a hydrogenation catalyst in a hydrogen atmosphere to form a mixture of compounds of the structural formulae:

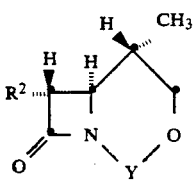

VIIα (alpha)

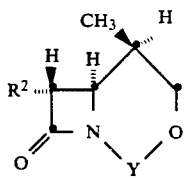

VIIβ (beta)

wherein the β/α epimeric molar ratio is greater than 1:

g) separating the β-epimer from the mixture;

h) contacting Compound VIIβ with an oxidizing agent to yield a compound of the structural formula:

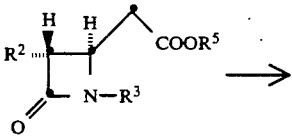

VIII wherein above: $R^2$ is independently selected from hydrogen, linear or branched $C_1$-$C_3$ alkyl, which can be substituted with fluoro, hydroxy or protected hydroxyl; $R^3$ is H or a protecting group and $R^3$ is H or $C_1$-$C_4$ alkyl.

DESCRIPTION OF THE INVENTION AND THE PREFERRED EMBODIMENTS

The basic invention process is best illustrated by reference to the following flow sheet:

FLOW SHEET

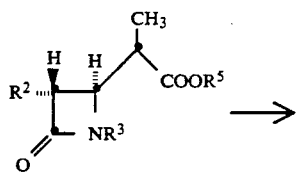

I

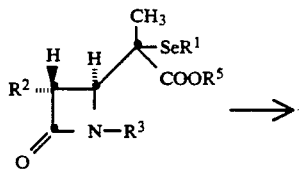

II

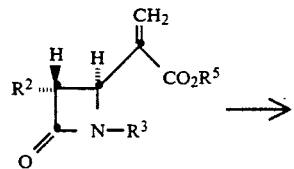

III

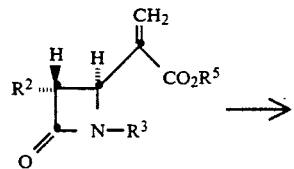

IV

-continued
FLOW SHEET

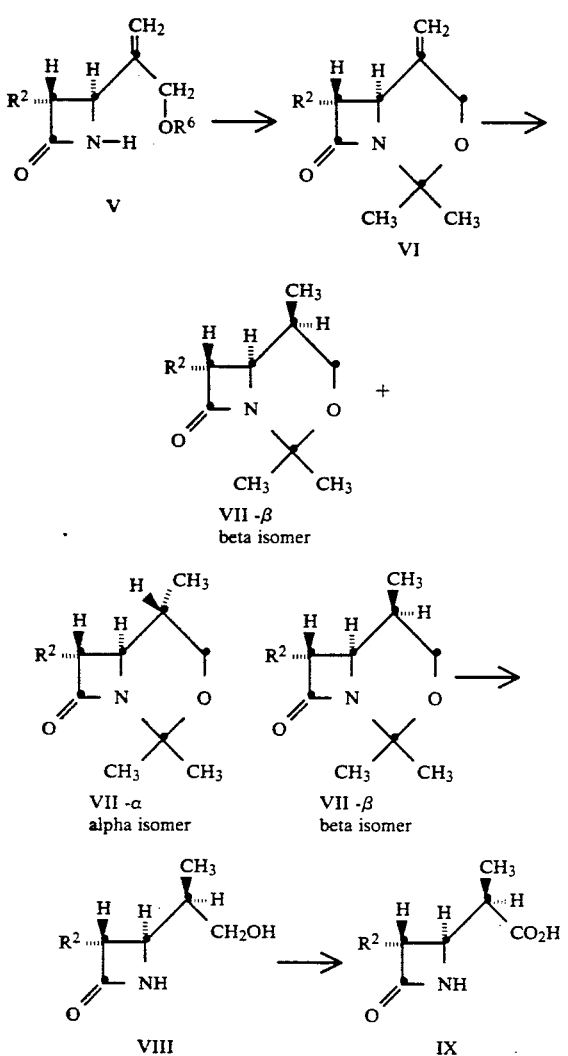

VII -β
beta isomer

VII -α
alpha isomer

VII -β
beta isomer

VIII

IX

The invention process is an improved process for producing the beta and alpha epimers VII-beta and VII-alpha in high overall yields starting with compound I. The novelty of the process resides primarily in the steps leading from structures III to V, in oxidizing the double-bonded selenium compound to form the terminal double bond of structure IV and then proceeding through reduction of the ester first while leaving the double bond intact.

The significance of the process can be seen from the fact that the overall yield in the process from structure I to IX is of the order of about 65%. Further, the steps leading from compound II to compound V can be carried out in 85% overall yield in a "one-pot" reaction sequence, greatly simplifying the process. Further significant aspects of the invention process are the improved alkylation conditions for preparing structure II and improved reduction conditions leading to structure VII.

In words relative to the above Flow Sheet, structure I is methylated in the alpha position to produce structure II, a mixture of the alpha and beta isomers. Use of a potassium proton abstracting agent increases the yield, eliminates the need for the use of hexamethylphosphoramide (HMPA), and increases the beta/alpha isomer ratio yield which allows the selenation step to yield structure III to proceed in higher yield. The step is carried out under dry and $O_2$-free conditions, preferably under nitrogen, by treating I with a potassium salt proton extracting agent such as $KN(SiMe_3)_2$ in an anhydrous solvent such as THF, glyme, diethylether, and the like, at a temperature of about $-78°$ to $-30°$ C. Preferably the proton abstracting agent is $KN(SiMe_3)_2$, the solvent is THF and the temperature is $-78°$ C. to $-50°$ C.

Structure I with the indicated stereochemistry where $R^2$ is (R,S) $CH_3CH(OR^4)$ in which $R^4$ is H or t-butyldimethylsilyl, is known and can be synthesized by the method described in the above-cited *Heterocycles* reference by D. Shih et al., hereby incorporated by reference for this particular purpose.

The selenation of II to III is conducted under dry and $O_2$-free conditions, preferably under nitrogen, by treating II with a proton-abstracting agent such as LDA (lithium diisopropylamide) in an anhydrous solvent such as THF (tetrahydrofuran), and in the absence of HMPA (hexamethylphosphoramide), followed by treating with a selenation agent. Other proton abstracting agents which can be used are lithium hexamethyldisilazide, NaH, lithium cyclohexylisopropylamide, and the like. Preferred is LDA. Other solvents which can be used in this particular step are glyme, diethylether, dimethylformamide, and the like. The solvent should be dry and inert under the reaction conditions and preferred is tetrahydrofuran.

The selenating agent used is a selenyl halide, preferably phenylselenyl chloride, and the reaction is carried out at $-78°$ C to $0°$ C. under nitrogen atmosphere for a period of time of about 1 to 8 hours to achieve a desired yield of the selenated compound III. A mixture of alpha and beta selenides is produced, but it is not absolutely necessary to perform a separation step since either diastereomer or a mixture can be used in the later oxidation step to produce the identical alpha-methylene compound IV.

The selenide III is then treated with an oxidizing agent such as hydrogen peroxide in THF solvent to form IV having the terminal double bond at the α-position to the B-lactam ring. Generally this step is conducted at about 0° to 100° C., for a period of time of about 1 to 24 hours. Other oxidizing agents which can be used include peroxyacetic acid, m-chloroperoxybenzoic acid, ozone, and $NaIO_4$ in solvents including methylene chloride, toluene, water and EtOH. Preferred oxidizing system is hydrogen peroxide in THF solvent.

The resulting methylene-ester IV is reduced to the primary alcohol V by a suitable reducing agent, including $BH_3.Me_2S$, and diisobutylaluminum hydride (DIBAL) in solvent THF, at a temperature of 0 to 65° C., for about 2 to 24 hours under a nitrogen atmosphere to achieve the alcohol. Other reducing agents such as lithium aluminum hydride and borane can also be used which are not detrimental to the beta-lactam ring.

Following the above reduction procedure, the ring nitrogen is deblocked, if a conventional blocking group is present, by the procedure of acid or base catalyzed hydrolysis, but not hydrogenation, and the lactam alcohol is joined together by reaction with a divalent bridging-protecting group as described herein such as 2,2-dimethoxypropane, or the like, in a suitable solvent and presence of a Lewis acid such as $BF_3.Et_2O$, p-toluenesulfonic acid, trifluoroacetic acid, chlorosulfonic acid to form VI. Other bridging-protecting agents which can also be used are cyclohexanone, p-methoxyacetophenone or its dimethylketal, or a diorganodichlorosilane such as d-ti-butyldichlorosilane. Preferred is 2,2-dimethoxypropane, reacted in methylene chloride solvent. Following cyclization the 1'-hydroxy group is deblocked by treating with tetrabutylammonium fluoride in DMF. The deblocking of the 1'-hydroxy group has been found to be highly favorable in obtaining a high ratio of β/α epimers in the subsequent reduction step.

Following the deblocking step, the reduction is carried out with Raney Nickel, preferably washed with ethyl acetate or other non-protic solvent, to yield a mixture of the β-methyl and α-methyl epimers VII, being VII-β and VII-α, respectively, with the β-methyl epimer predominating. The resulting β- and α-isomers can be separated by high pressure liquid chromatography (HPLC), as for example, on a Pre PAK 500/silica column as in conventional practice or by fractional crystallization or the like to obtain the β-epimer in high purity.

The β-isomer once obtained in high purity, can be converted to VIII and then IX by using the methods described in U.S. Pat. No. 4,234,596 hereby incorporated by reference for that purpose.

As is seen, the α-exocyclic methylene double bond of VI is hydrogenated to produce the β-methyl isomer VII-B and the α-methyl isomer VII-α. The hydrogenation conditions employed are conventional in the art, and it was found that the hydrogenation of structure VI, particularly where $R^2$ is

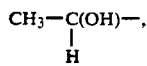

gave rise selectively to the β-methyl isomer in the resulting product mixture which contained a β/α epimer molar ratio of greater than 1 and upwards of 15:1.

The catalyst employed in the hydrogenation is Raney nickel, i.e. W-2, W-4, W-6, or other grades as prepared by conventional procedures, but including a final wash with a non-protic solvent including ethyl acetate, THF, Et₂O, t-butylmethyl ether, toluene and the like. A preferred catalyst for use in the process is Raney Nickel as produced by the conventional process described in the reference L. F. Fieser, "Reagents for Organic Synthesis", Vol. 1, p. 723 (John Wiley & Sons, New York), incorporated by reference herein for that purpose, in which said catalyst is subsequently washed with ethyl acetate.

Solvents for Structure VI which can be used for the hydrogenation in the process should be inert under the reaction conditions and have a boiling point in the temperature range of about 50°-100° C. for adequate temperature to be achieved during the process. Representative examples of solvents which can be used in the process include protic and aprotic solvents such as $C_1$-$C_3$ alcohols, $C_3$-$C_6$ alkyl carboxylic esters, $C_4$ cyclic mono- and diethers, and derivatives thereof, which can contain substituents such as lower alkyl and alkoxy, inert under the hydrogenation conditions. Representative examples include EtOH, MeOH, MeOAc, EtOAc, dioxane, tetrahydrofuran and the like. A preferred solvent in the process is EtOH.

Concentrations of VI in the solvent can range from 0.001 to 1 molar and preferably 0.1 to 1 molar.

Temperature employed in the hydrogenation process can range from −78° C. up to the boiling point of the solvent. The preferred temperature range for conducting the process is about 25° C.

Pressure employed in the process can be anywhere from one atmosphere to several atmospheres suitable for standard olefin reduction conditions. Preferred is a pressure of about 0–40 psig and particularly about 40 psig, containing a substantially hydrogen atmosphere. The hydrogen atmosphere can of course contain other gases which are either reducing or inert under the reaction conditions such as small amounts of carbon monoxide or carbon dioxide and the like. Preferably the atmosphere used in the hydrogenation is substantially a hydrogen atmosphere.

The time involved in the hydrogenation is that sufficient under the reaction conditions to obtain substantial catalytic hydrogenation of structural formula VI to obtain a resulting β/α epimer molar ratio of greater than 1. β/α epimer molar ratios of substantially greater than 1 are achieved, being generally 1.5 and above and can approach a ratio of 15:1 via the hydrogenation step.

The compounds encompassed by structural Formula VI include those compounds wherein $R^2$ is independently selected from H, linear or branched $C_1$-$C_3$ alkyl, which can be substituted with fluoro, hydroxy or protected hydroxy. The hydroxy protecting groups included herein are known in the antibiotic art, are removable by acid or base hydrolysis, and include, inter alia, trialkylsilicon groups such as t-butyldiphenylsilyl, triphenylsilyl, isopropyldimethylsilyl or t-butyldimethylsilyl.

A preferred hydroxy protecting silyl group, e.g. t-butyldimethylsilyloxy can be formed by reacting the hydroxy group, e.g. 1-hydroxyethyl, with t-butyldimethylsilyl chloride in a dry solvent such as methylene chloride, DMF, or other inert solvents, in the presence of an acid acceptor, e.g. triethylamine or imidazole, at −20 to 25° C. for a period of 1-2 hours and then isolating and purifying the desired protected hydroxy compound by conventional methods.

When desired to remove the protecting group, such as prior to hydrogenation, the protected silyloxy can be treated with fluoride (or acid), e.g. with tetrabutylammonium fluoride in tetrahydrofuran in dimethylformamide solvent at room temperature for 1-2 hours. Isolation and purification of the resulting hydroxy compound can be accomplished by conventional procedures. Generally, in the hydrogenation step of the methylene double bond, it is preferred to deblock the hydroxy group when present in $R^2$ prior to the hydrogenation.

Representative examples of $R^2$ include H, CH₃—, CH₃CH₂—, (CH₃)₂CH—, HOCH₂—, CH₃CHOH—, CH₃CH[OSi[C(CH₃)₃](CH₃)2]—, (CH₃)₂COH—, FCH₂—, F₂CH—, F₃C—, CH₃CHF—, CH₃CF₂—, (CH₃)₂CF—, CH₃CH₂CHOH— and FCH₂CHOH—. Preferred is where $R^2$ is CH₃CHOH—.

Y is a bridging-protecting group derived from an aldehyde, ketone or organosilicon compound, or equivalent thereof, including acetals, ketals, and the like and includes

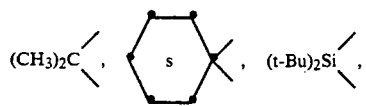

-continued

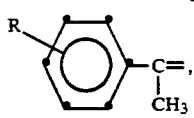

and substituted derivatives thereof,
wherein said substituents R are inert during the subject process described herein and include, inter alia, $C_1-C_4$ lower alkyl and alkoxy.

Representative examples of aldehydes, ketones and organosilicon compounds which are precursors for Y include those which are known in the antibiotic art, e.g., acetone, 2,2-dimethoxypropane, cyclohexanone, 1,1-dimethoxycyclohexane, methylethylketone, 2,2-diethoxy-n-butane, acetaldehyde, acetaldehyde dimethylacetal, acetophenone, p-methoxyacetophenone, dichlorodimethylsilane, dichlorodiphenylsilane, dichloroethylphenylsilane, dichloro-di-t-butylsilane and the like. A preferred reagent for forming the Y moiety is 2,2-dimethoxypropane wherein the Y moiety is formed by reacting the deblocked amino alcohol of structure V for example with 2,2-dimethoxypropane in the presence of a catalyst such as boron trifluoride etherate, toluenesulfonic acid, or the like in a solvent such as methylene chloride, ether, chloroform, dioxane or the like at a temperature of from $-10°$ C. to $35°$ C. for from a few minutes to 1 hour.

The bridging-protecting group Y, not readily removable by hydrogenation, is removable by acid or base hydrolysis as described in the reference U.S. Pat. No. 4,234,596, hereby incorporated by reference for that purpose.

Structure VI is derived as described above from the reaction of ketone, aldehyde or organosilicon compound with the deblocked amino-alcohol V, where $R^3$ and $R^6$ are H:

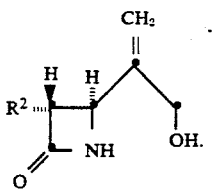

Representative examples of structure VI include:

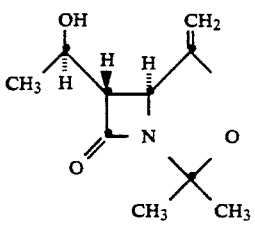

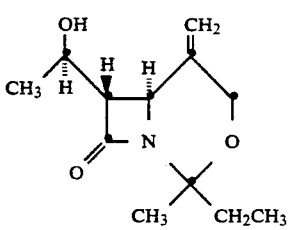

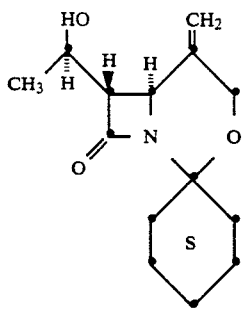

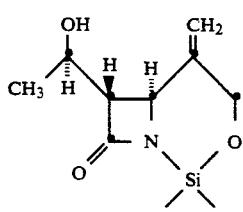

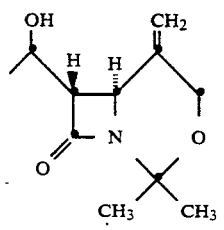

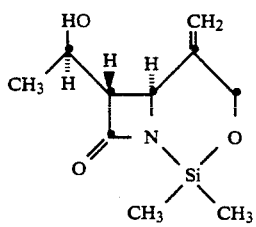

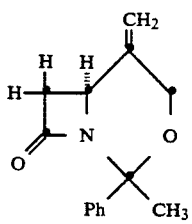

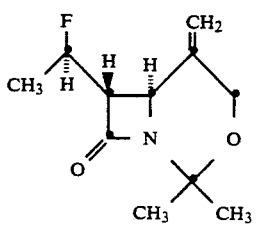

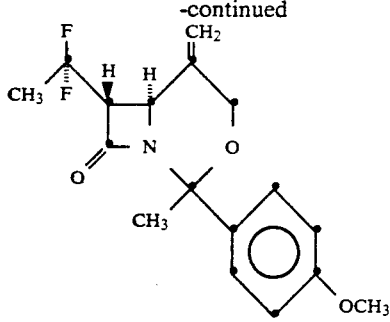

Further examples of Structure VI for illustration purposes are given below in the Table indicating specified values chosen for R² and bridging-protecting group Y.

TABLE

| Compound | R² | Y |
| --- | --- | --- |
| 1 | H | (t-Bu)₂Si= |
| 2 | H | Ph₂Si= |
| 3 | H | [thiacyclohexylidene] |
| 4 | H | (CH₃)₂C= |
| 5 | CH₃ | (CH₃)₂C= |
| 6 | CH₃ | [thiacyclohexylidene] |
| 7 | CH₃ | (CH)₃Si= |
| 8 | CH₃ | Ph(CH₃CH₂)Si= |
| 9 | CH₃CH₂CH₂ | Ph(CH₃CH₂)Si= |
| 10 | CH₃CH₂CH₂ | Ph₂Si= |
| 11 | CH₃CH₂CH₂ | CH₃CH₂C= / CH₃ |
| 12 | CH₃CH₂CH₂ | [phenyl]-C(CH₃)= |
| 13 | (CH₃)₂CH | (CH₃)₂C= |
| 14 | (CH₃)₂CH | [thiacyclohexylidene] |
| 15 | (CH₃)₂CH | (t-Bu)₂Si= |
| 16 | (CH₃)₂CH | Ph₂Si= |
| 17 | HOCH₂ | Ph₂Si= |
| 18 | HOCH₂ | (CH₃)(CH₃CH₂)Si= |
| 19 | HOCH₂ | MeO-[phenyl]-C(CH₃)= |
| 20 | HOCH₂ | (CH₃)₂C= |
| 21 | (CH₃)₂COH— | (CH₃)₂C= |
| 22 | (CH₃)₂COH— | CH₃CH₂—C= / CH₃ |

TABLE-continued

| Compound | R² | Y |
| --- | --- | --- |
| 23 | (CH₃)₂COH— | (CH₃)₂Si= |
| 24 | (CH₃)₂COH— | Ph₂Si= |
| 25 | FCH₂— | Ph₂Si= |
| 26 | FCH₂— | (t-Bu)₂Si= |
| 27 | FCH₂— | [phenyl]-C(CH₃)= |
| 28 | FCH₂— | [thiacyclohexylidene] |
| 29 | F₂CH | [thiacyclohexylidene] |
| 30 | F₂CH | (CH₃)₂C= |
| 31 | F₂CH | Ph₂Si= |
| 32 | F₂CH | (t-Bu)₂Si= |
| 33 | F₃C | (t-Bu)₂Si= |
| 34 | F₃C | (CH₃)₂Si= |
| 35 | F₃C | [phenyl]-C(CH₃)= |
| 36 | F₃C | MeO-[phenyl]-C(CH₃)= |
| 37 | (CH₃)₂CF | MeO-[phenyl]-C(CH₃)= |
| 38 | (CH₃)₂CF | (CH₃)₂C= |
| 39 | (CH₃)₂CF | Ph₂Si= |
| 40 | (CH₃)₂CF | (CH₃)₂Si= |

The structures and formulae representative of Structure VI given in the above Table are not meant to be limiting and other combinations of R² and Y and their resulting species of Structure VI which will be obvious to one skilled in the art from this disclosure are also deemed to be included within the scope of the invention.

A preferred compound of structure VI for use in the process is:

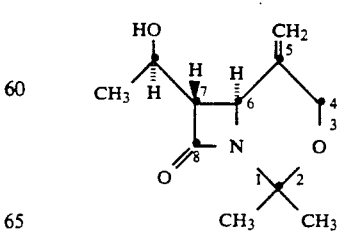

A synthesis of a species of general structure VI is given below in the Flow Sheet for converting the monocylic β-lactam ring system into the bicyclic system, 8-oxo-3-oxa-1-azabicyclo [4.2.0] octane with the exocyclic methylene group position 5 (see above) and a 1-hydroxyethyl radical at position 7.

By the same general procedure, the compounds encompassed by Structure VI, where $R^2$ and Y have other values disclosed herein, within the claimed definition, are also obtained.

FLOW SHEET

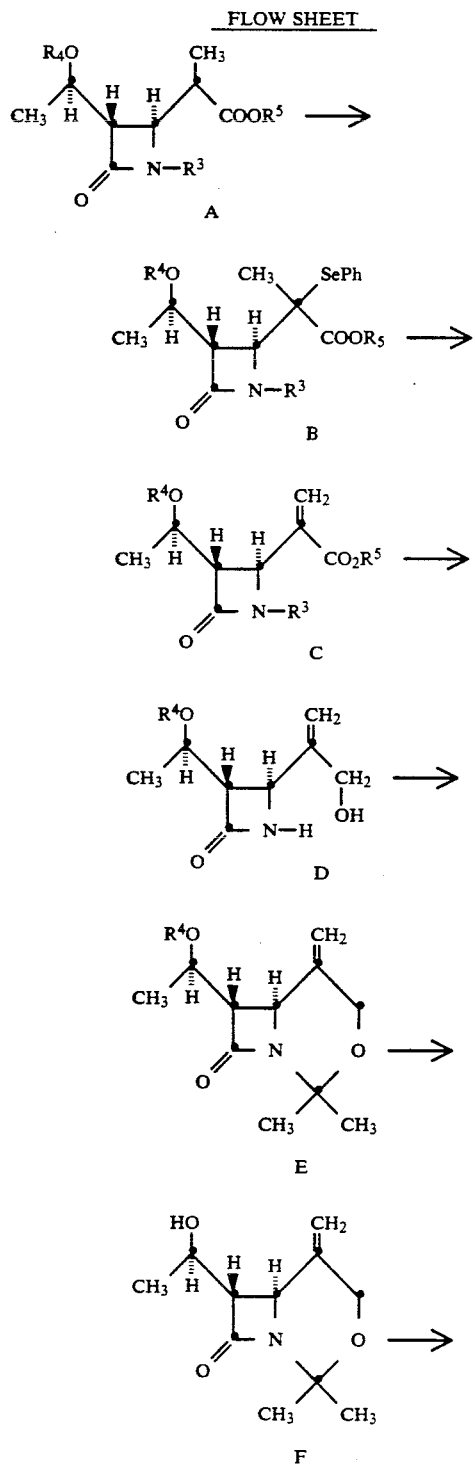

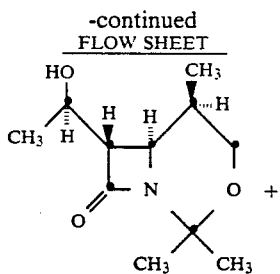

G-β beta isomer

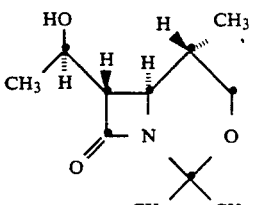

G-α alpha isomer

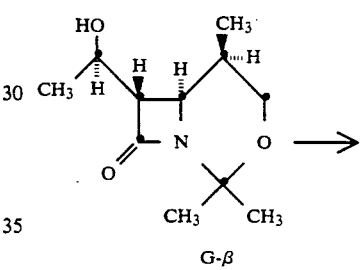

G-β beta isomer

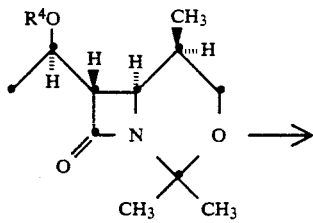

H

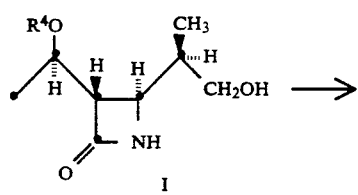

I

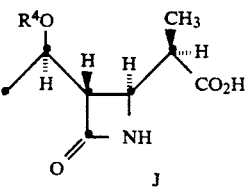

J

In words relative to the above Flow Sheet, starting compound A with the indicated sterochemistry where $R^4$ is H or t-butyldimethylsilyl, is known and can be synthesized by the method, described above in the instant process and in the above-cited *Heterocycles* reference, hereby incorporated by reference for this particular purpose.

The selenation of A to B is conducted under dry and $O_2$-free conditions by treating A with a proton-abstracting agent such as LDA (lithium diisopropylamide) in an anhydrous solvent such as THF (tetrahydrofuran) at $-78°$ C. to $0°$ C. under nitrogen atmosphere for a period of time of about 1 to 8 hours followed by treating with a selenation agent such as phenylselenyl chloride to achieve a desired yield of the selenated compound B. A mixture of alpha and beta selenides is produced, but it is not necessary to perform a separation step since either diastereomer or a mixture can be used in the later oxidation step to produce the methylene compound.

The selenide-ester B is then treated with an oxidizing agent such as hydrogen peroxide in THF solvent to form C having the terminal double bond at the α-position to the B-lactam ring. Generally this step is conducted at about $0°$ to $100°$ C., for a period of time of about 1 to 24 hours.

The methylene-ester C is reduced to the primary alcohol D by a suitable reducing agent, preferably diisobutylaluminum hydride (DIBAL) in solvent THF, at a temperature of 0 to $65°$ C., for about 2 to 24 hours under a nitrogen atmosphere to achieve the alcohol.

Following the above reduction procedure the amino alcohol is joined together by reaction with a divalent bridging-protecting group as described herein such as 2,2-dimethoxypropane, or the like, in a suitable solvent and presence of a Lewis acid such as $BF_3.Et_2O$, p-toluenesulfonic acid, chlorosulfonic acid to form E. Following cyclization, the 1'-hydroxy group is deblocked by treating with tetrabutylammonium fluoride in DMF to form F. The deblocking of the 1'-hydroxy group has been found to be highly favorable in obtaining a high ratio of β/α isomers in the subsequent reduction step.

Following the deblocking step to yield F, the reduction is carried out as described hereinabove with Raney Nickel, preferably washed with ethyl acetate, to yield a mixture of the β-methyl and α-methyl isomers G, being G-β and G-α, respectively, with the β-methyl isomer predominating. The resulting β- and α-isomers can be separated by high pressure liquid chromatography (HPLC), as for example, on a Pre PAK 500/silica column as in conventional practice or by fractional crystallization or the like to obtain the β-isomer in high purity.

The β-isomer once obtained in high purity,. can be converted to I and then J by using the methods described in U.S. Pat. No. 4,234,596 hereby incorporated by reference for that purpose.

The reaction G-β→H establishes the blocking group $R^4$ and is typically accomplished by treating G-β with a base such as an alkali metal hydroxide, lithium diisopropyl amide, 4-dimethyl-aminopyridine, or n-butyllithium in a solvent such as methylene chloride, ether, THF, dioxane, DMF, DMSO or the like, followed by treatment with an acyl halide of choice such as an alkanoyl, aralkanoyl or nuclear substituted aralkanoyl, or alkyl, aryl or aralkyl, substituted aralkyl or substituted aryl haloformate such as allylchloroformate or p-nitrobenzylchloroformate or the like at a temperature of from $-78°$ C. to $25°$ C. for from 1-24 hours.

Alternatively, the protecting group $R^{14}$ may be a triorganosilyl group, such as t-butyldimethylsilyl, t-butyldiphenylsilyl, triphenylsilyl, isopropyldimethylsilyl, for example, or may be 3,4-dimethoxybenzyl, for example. Typically $R^{14}$ is established by treating G-β in a solvent such as $CH_2Cl_2$, dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from $-20°$ to $25°$ C. for from 0.5 to 24 hours in the presence of a base such as triethylamine, diisopropylethylamine, or imidazole or 4-dimethylaminopyridine.

The de-blocking reaction H→I is typically conducted by acid hydrolysis such as aqueous acetic acid at a temperature of from $25°$ C. to $75°$ C. for from 5 minutes to 3 hours.

The oxidation of I to J is accomplished by treating I in a solvent such as acetone or the like with Jones reagent at from $-78$ to $25°$ C. for from one minute to 2 hours. Alternatively, the conversions H to I to J may be done in one step by treatment of H as above with Jones reagent to give J directly.

The carboxylic acid J can then be treated for example, by the method described in the above-cited *Heterocycles* reference and U.S. Pat. No. 4,383,946 and 4,309,346, all hereby incorporated by reference for this purpose, to arrive at subsequent active 1-β-methylcarbapenum antibiotics, including (−)-(1R,5S,6S)-2-(2-N,N-dimethylamino-2-iminoethylthio)-6-[(1R)-1-hydroxyethyl]-1-methylcarbapen-2-em-3-carboxylic acid, useful as described hereinabove.

Preferred process for selectively reducing an exocyclic α-methylene ring double bond of the invention comprises the step of contacting the compound:

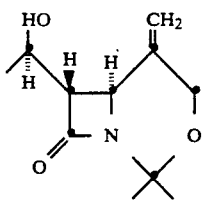

in an organic solvent therefor as described hereinabove, with a hydrogen atmosphere at about 40 psig reaction pressure with Raney nickel catalyst for a time sufficient to obtain a mixture of α-methyl and β-methyl isomers in a β to α epimeric molar ratio of greater than 1.

Methods of synthesis are given below in the *Diagram, Schemes*, and discussion, for other starting compounds A, where radical $R_2$ on the beta lactam ring is chosen from other groups within the claimed definition therefor. The methods are taken from U.S. Pat. No. 4,309,346 and U.S. Pat. No. 4,383,946, which are incorporated by reference specifically for this purpose.

DIAGRAM 1

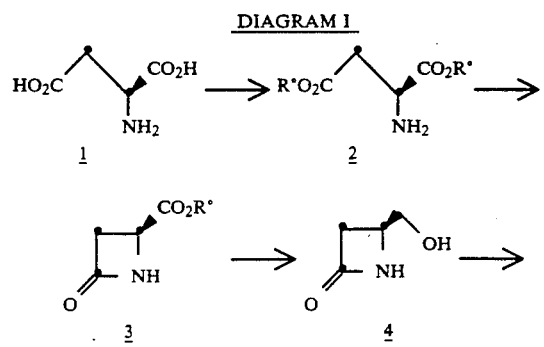

-continued
DIAGRAM I

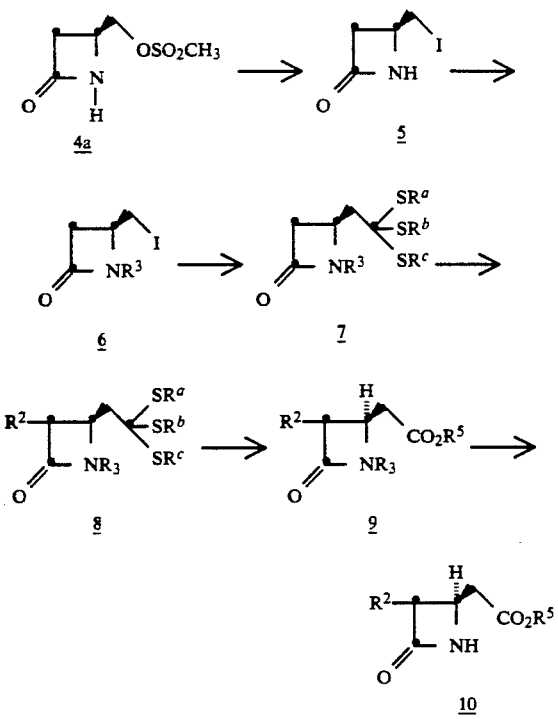

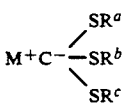

In words relative to the above diagram, L-aspartic acid 1 is esterified according to well known procedures. R° is a protecting group such as benzyl, methyl, ethyl, isopropyl or the like. Typically 1 in a solvent such as benzene, toluene, chloroform or the like is treated with an esterifying agent such as benzyl alcohol, methanol, ethanol, isopropanol, or the like in the presence of p-toluene sulfonic acid, HCl, HBr, or the like at a temperature of from 0 to 100° C. for from 1 to 24 hours to achieve the desired establishment and hence protection of the carboxyl functions. The resulting species 2 in a solvent such as ether, THF, DME or the like is treated with trimethylchlorosilane, or the like followed by treatment with EtMgBr, MeMgI, $\phi$MgBr, t-BuMgCl, or the like at a temperature of from $-40$ to 50° C. for from 1 to 72 hours to provide azetidinone 3. Reduction of species 3 with a reducing agent such as NaBH$_4$, or the like in a solvent such as methanol, ethanol, isopropanol or the like at a temperature of from $-10$ to 40° C. for from 1 to 6 hours provides 4. (For purposes here, the symbols: Et, Me, $\phi$, iPr, and t-Bu stand for: ethyl, methyl, phenyl, isopropyl, and tert-butyl, respectively.)

Treatment of 4 in a solvent such as methylene chloride, CHCl or the like with methane sulfonyl chloride, methane sulfonic anhydride or the like in the presence of a base such as Et$_3$N, iPr$_2$NEt, or the like followed by treatment with a stoichiometric to 5-fold excess of sodium iodide in acetone yields 5 via 4a.

The transformation 5 6 establishes the protecting group R$^3$ which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically R$^3$ is established by treating 5 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from $-20°$ to 25° C. for from 0.5 to 24 hours in the presence of a base such as triethylamine, diisopropylethylamine, or imidazole.

The transformation 6→7 is accomplished by treating 6 in a solvent such as tetrahydrofuran, dimethoxyethane, diethylether or the like with a carbanion generically represented by the following structure:

$$M^+C{-}{\overset{\displaystyle SR^a}{\underset{\displaystyle SR^c}{-}SR^b}}$$

wherein M is a metal cation such as lithium, potassium, copper or magnesium, for example, and R$^a$, R$^b$ and R$^c$ are selected from alkyl, aryl or aralkyl such as methyl, ethyl, benzyl, methoxybenzyl, trityl and phenyl, for example, at a temperature of from $-100$ to 0° C. and from 0.5 to 4 hours.

Typically, the carbanion reagent is prepared prior to addition of substrate 6 on treatment of the triorganothiomethane with a strong base such as n-butyllithium, t-butyllithium, phenyllithium, lithium diisopropylamide (LDA) or the like.

Resulting intermediate 7 can be mono-, or dialkylated at ring position 3. Alkylation of 7 provides 8. Typically, 7 is treated with a strong base such as lithium diisopropylamide, lithium 2,2,6,6-tetramethylpiperidide, potassium hydride, lithium hexamethyldisilazide, phenyllithium or the like in a solvent such as tetrahydrofuran (THF), hexamethylphosphoramide, ether, dimethoxyethane, and the like at a temperature of from $-80°$ C. to 0° C. whereupon the alkylating agent of choice, R$^2$X° is added (X° is chloro, iodo or bromo); alternatively the alkylating agent may be R$^2$-tosylate, R$^2$-mesylate or an aldehyde or ketone such as acetaldehyde to provide monoalkylated species 8.

The eventual 6-substituents (nomenclature relative to final, bicyclic structure) can also be established by direct acylation using an acylating agent such as N-acyl imidazole or the like. Such N-acyl imidazole acylating reagents are listed below. Also given below is a detailed description of this second approach for establishing R$^2$.

The following list is representative of useful alkylating agents for establishing R$^2$, according to the above scheme: 7 8 (this will be referred to as Scheme I, to be distinguished from Scheme II, below, which involves acylation):

Alkylating Agents

CH$_3$CHO

CH$_2$O

CH$_3$I

CH$_3$COCH$_3$

CH$_3$CH$_2$Br (CH$_3$)$_2$CHBr

CH$_3$CH$_2$CHO

CF$_3$CHO

CHF$_2$CHO

CH₂FCHO

F₂CHI

F₃CI

CH₃CF₂I

The fluoro compounds CH₃CHF—, and F—CH₂—, can be prepared from the corresponding hydroxy compounds by treating the hydroxy compound with DAST ™, diethylaminosulfur trifluoride, in an inert solvent such as THF, at a temperature of −78 to 25° C. under an inert atmosphere for a period of about 1 to 2 hours. As mentioned above, the 6-substituents may also be established by acylation. Utilization of such acylating agents may be demonstrated in the following manner with regard to a preferred starting, or intermediate, material 8.

SCHEME II

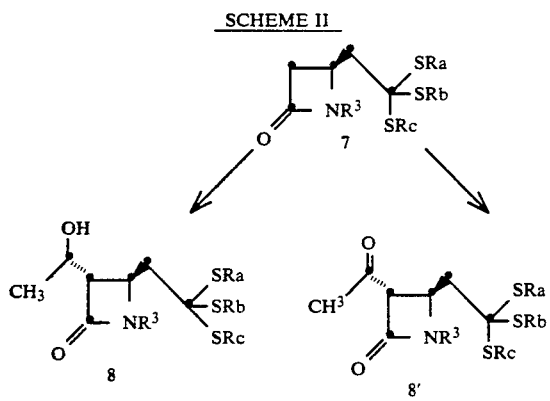

The alkylation 7→8, is accomplished as previously described, by treating 7 in a solvent such as tetrahydrofuran, dimethoxyethane, diethylether, hexamethylphosphoramide, at a temperature of from −100° to −20° C. with a strong base such as lithium diisopropylamide, lithium hexamethyldisilazide, lithium 2,2,6,6-tetramethylpiperidide, potassium hydride or the like followed by the addition of an equivalent to 10 fold excess of an aldehyde. This reaction gives a mixture of isomers from which the desired trans-R form 8 can be conveniently separated by known methods of chromatography or crystallization. Intermediate 7 may proceed directly to 8 as indicated above, Scheme I, or it may take the circuitous path via 8'. The direct acylation, to 8' is accomplished by treating 7 with two or more equivalents of a base such as lithium diisopropylamide, lithium hexamethyldisilazide, lithium 2,2,6,6-tetramethylpiperidide, in a solvent such as tetrahydrofuran, diethylether, or dimethoxyethane, for example, at a temperature of from −100 to −20° C. with an acylating agent such as N-acyl imidazole or the like. Addition of the 7 plus base mixture to the acylating agent is preferred.

Representative acylating agents for this scheme 7→8'→8 are listed below.

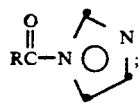

R=CH₃, CH₃CH₂, CH₃OCH₂, CF₃, CF₂H, CH₂F.

Further with respect to Scheme II, the reduction 8'→8 is accomplished by contacting the ketone with a reducing agent such as potassium tri(sec-butyl)borohydride, lithium tri(sec-butyl) borohydride, sodium borohydride, sodium tris (methoxyethoxy)aluminum hydride, lithium aluminum hydride or the like in a solvent such as diethylether, tetrahydrofuran, toluene or the like at a temperature of from −78° to 25° C. The reaction can conveniently be conducted in the presence of an added complexing salt such as potassium iodide, magnesium bromide or the like.

In a similar manner, unresolved 8 (cis and trans) may be oxidized to 8' for reduction to 8 as indicated above:

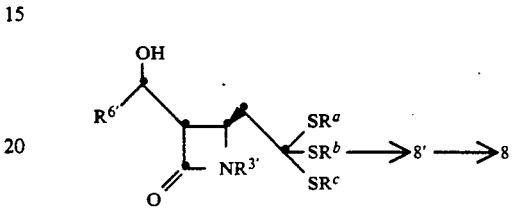

The oxidation is accomplished with an oxidizing agent such as dipyridine chromium (VI) oxide, trifluoroacetic anhydride-dimethylsulfoxidetriethylamine, pyridinium dichromate, acetic anhydride-dimethylsulfoxide in a solvent such as methylene chloride, acetonitrile, or the like at a temperature of from −78 to 25° C. for from 5 minutes to 5 hours.

Now return to the main scheme of synthesis, Diagram I, and the transformation 8→9, which is accomplished by treating 8 in a solvent such as methanol, ethanol, isopropanol, water or the like at a temperature of from 0 to 80° C. with a Lewis acid such as mercuric chloride, silver tetrafluoroborate, thallium trinitrate or the like. The value of R⁵ is determined by the identity of the alcohol taken in reaction.

The triorganylsilyl protecting group R³ may then be removed from 9 to give 10 by treatment with fluoride, e.g. tetrabutylammonium fluoride in tetrahydrofuran, in a solvent such as tetrahydrofuran, dimethylformamide, ether or the like at a temperature of from −78° to 25° C. for from 1 minute to 2 hours.

The mono-alkylated products 8 through 10, in which R² does not contain a chiral center, will exist as a mixture of cis and trans structures:

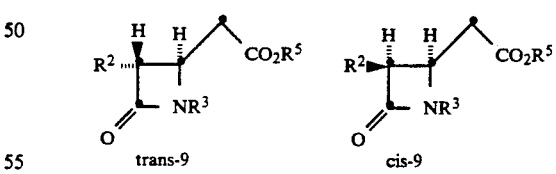

the configurational isomerism referring to the 3- and 4-hydrogen atoms on the ring. The desired isomer, trans-8 through 10, can be obtained by known methods in the art including crystallization and chromatography. The resulting trans-10 form can be used directly in producing the desired 1-betamethyl intermediates, by following the procedure in *Heterocycles, supra*, wherein trans-10 is treated with two equivalents of lithium diisopropylamide (LDA) in THF containing one equivalent of HMPA (hexamethylphorphoramide) at −78° C. followed by excess methyl iodide yields a mixture of the alpha and beta methyl isomers which is then selenated and carried through the remaining steps as indicated in the Flow Sheet.

An alternate route for producing the intermediate:

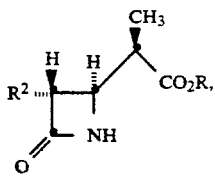

where $R^2=CH_3CHOH-$, is given in U.S. Pat. No. 4,206,219, hereby incorporated by reference for this particular purpose.

Also a subject of the instant invention are the compositions produced in the above-described process of forming the exocyclic double bond leading to the desired 1-β-methylcarbapenem intermediates being compositions of the Formula:

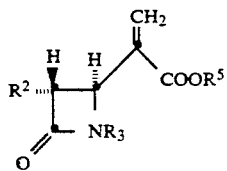

wherein $R^2$ is independently selected from hydrogen, linear or branched $C_1$-$C_3$ alkyl, which can be substituted with fluoro, hydroxy or protected hydroxy, $R^3$ is hydrogen or a protecting group, $R^5$ is a protecting group, or $C_1$-$C_4$alkyl. The protecting group $R^3$ is also removable by acid or base hydrolysis and includes the triorganosilyl groups known in the art as also represented by $R^4$ in Structure A.

The compositions include these wherein said $R^2$ is independently selected from H, $CH_3-$, $CH_3CH_2-$, $(CH_3)_2CH-$, $HOCH_2-$, $CH_3CHOH-$, $(CH_3)_2COH-$, $FCH_2-$, $F_2CH-$, $F_3C-$, $CH_3CHF-$, $CH_3CF_2$, $(CH_3)_2CF-$, $CH_3CH_2CHOH-$, $FCH_2CHOH-$, and wherein said Y includes

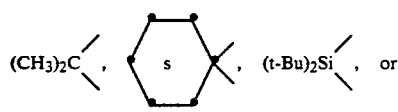

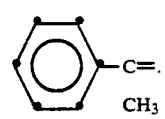

Representative Examples of Structure IV which are adequately illustrated hereinabove and need not be reiterated but are incorporated by reference herein as supplementing disclosure.

Representative Examples of Structure IV where $R^3$ and $R^6$ have other values than Y are presented in the following Table:

TABLE

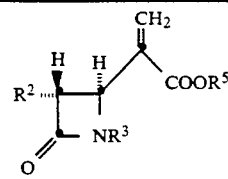

| Compound | $R^2$ | $R^3$ | $R^5$ |
|---|---|---|---|
| 1 | H | H | $CH_3$ |
| 2 | $CH_3$ | H | $CH_3$ |
| 3 | $CH_3CH_2$ | H | $CH_3$ |
| 4 | $CH_3CH_2CH_2$ | H | $CH_3$ |
| 5 | $(CH_3)_2CH$ | H | $CH_3$ |
| 6 | $HOCH_2$ | H | $CH_3$ |
| 7 | $CH_3CHOH$ | H | $CH_3$ |
| 8 | $(CH_3)_2COH$ | H | $CH_3$ |
| 9 | $DMTBS-OCH_2$ | H | $CH_3$ |
| 10 | $DPTBS-OCH_2$ | H | $CH_2CH_3$ |
| 11 | $TPS-OCH_2$ | H | $CH_2CH_3$ |
| 12 | $IPDMS-OCH_2$ | H | $CH_2CH_3$ |
| 13 | $CH_3CH(O-DMTBS)-$ | H | $CH_2CH_3$ |
| 14 | $CH_3CH(O-DPTBS)-$ | H | $CH_2CH_3$ |
| 15 | $CH_3CH(O-TPS)$ | H | $CH_2CH_3$ |
| 16 | $CH_3CH(O-IPDMS)$ | H | $CH_2CH_3$ |
| 17 | $(CH_3)_2C(O-DMTBS)$ | H | $CH_2CH_3$ |
| 18 | $(CH_3)_2C(O-DPTBS)$ | H | $CH_2CH_3$ |
| 19 | $(CH_3)_2C(O-TPS)$ | H | $CH_2CH_3$ |
| 20 | $(CH_3)_2C(O-IPDMS)$ | H | $CH(CH_3)_2$ |
| 21 | $FCH_2$ | H | $CH(CH_3)_2$ |
| 22 | $F_2CH-$ | H | $CH(CH_3)_2$ |
| 23 | $F_3C-$ | H | $CH(CH_3)_2$ |
| 24 | $CH_3CHF$ | H | $CH(CH_3)_2$ |
| 25 | $CH_3CF_2$ | H | $CH(CH_3)_2$ |
| 26 | $(CH_3)_2CF-$ | H | $(CH_2)_3CH_3$ |
| 27 | H | IPDMS | $(CH_2)_3CH_3$ |
| 28 | $CH_3$ | IPDMS | $(CH_2)_3CH_3$ |
| 29 | $CH_3CH_2$ | IPDMS | $(CH_2)_3CH_3$ |
| 30 | $CH_3CH_2CH_2$ | IPDMS | $(CH_2)_3CH_3$ |
| 31 | $(CH_3)_2CH$ | DMTBS | $(CH_2)_3CH_3$ |
| 32 | $HOCH_2$ | DMTBS | $C(CH_3)_4$ |
| 33 | $CH_3CHOH$ | DMTBS | $C(CH_3)_4$ |
| 34 | $(CH_3)_2COH$ | DMTBS | $C(CH_3)_4$ |
| 35 | $DMTBS-OCH_2$ | DPTBS | $C(CH_3)_4$ |
| 36 | $DPTBS-OCH_2$ | DPTBS | $C(CH_3)_4$ |
| 37 | $TPS-OCH_2$ | DPTBS | $C(CH_3)_4$ |
| 38 | $IPDMS-OCH_2$ | DPTBS | $C(CH_3)_4$ |
| 39 | $CH_3CH(O-DMTBS)$ | TPS | $C(CH_3)_4$ |
| 40 | $CH_3CH(O-DPTBS)$ | TPS | $C(CH_3)_4$ |
| 41 | $CH_3CH(O-TPS)$ | TPS | $C(CH_3)_4$ |
| 42 | $CH_3CH(O-IPDMS)$ | TPS | $C(CH_3)_4$ |
| 43 | $(CH_3)_2C(O-DMTBS)$ | H | $C(CH_3)_4$ |
| 44 | $(CH_3)_2C(O-DPTBS)$ | H | $(CH_2)_2CH_3$ |
| 45 | $(CH_3)_2C(O-TPS)$ | H | $(CH_2)_2CH_3$ |
| 46 | $(CH_3)_2C(O-IPDMS)$ | H | $(CH_2)_2CH_3$ |
| 47 | $FCH_2$ | IPDMS | $(CH_2)_2CH_3$ |
| 48 | $F_2CH$ | IPDMS | $(CH_2)_2CH_3$ |
| 49 | $F_3C$ | IPDMS | $(CH_2)_2CH_3$ |
| 50 | $CH_3CHF$ | DMTBS | $(CH_2)_2CH_3$ |
| 51 | $CH_3CF_2$ | DMTBS | $(CH_2)_2CH_3$ |
| 52 | $(CH_3)_2CF$ | DMTBS | $(CH_2)_2CH_3$ |

The abbreviations used:
IPDMS = isopropyldimethylsilyl
DMTBS = dimethyl-t-butylsilyl
DPTBS = diphenyl-t-butylsilyl
TPS = triphenylsilyl The structures and formulas representative of Structure IV given in the above Table are not meant to be limiting, and other combinations of $R^2$, $R^3$ and $R^5$ and their resulting species of Structure IV, which will be obvious to one skilled in the art in light of this disclosure are also deemed to be included within the scope of the invention.

Preferred compositions of Structure V are:

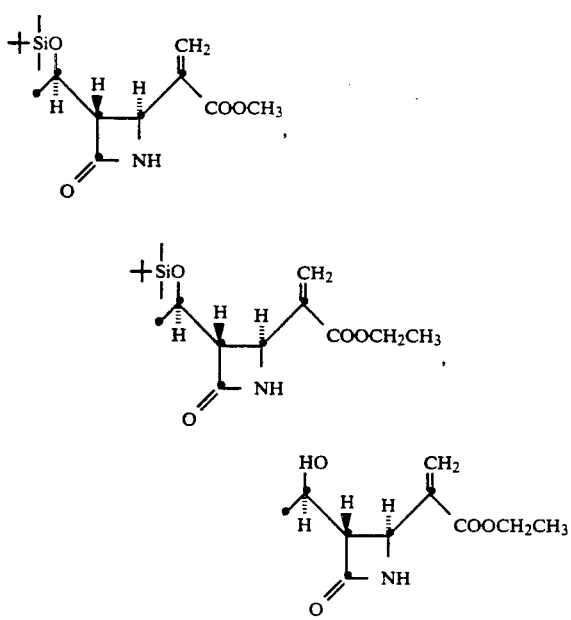

Also intermediate compositions in the invention process are the compositions of the Structural formula:

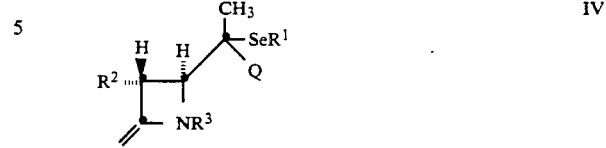

wherein $R^2$ is described hereinabove, $R^3$ is hydrogen or a blocking group, Q is hydroxymethyl, carboxy or $C_1$-$C_4$ alkoxycarbonyl, and $R^1$ is $C_1$-$C_4$ alkyl, $C_6$-$C_{10}$ aryl, heteroaryl, said aryl and heteroaryl can contain substituents including $C_1$-$C_4$ alkyl and alkoxy, nitro and the like, which are inert under the reaction conditions. By the term "substituted phenyl" is meant substituents inert under the reaction conditions leading to the synthesis of structure I and include $C_1$-$C_4$ alkyl, alkoxy, nitro and the like.

Representative Examples of Structure III are given in the following Table.

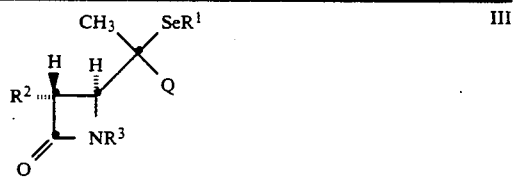

| Compound | $R^1$ | $R^2$ | $R^3$ | Q |
|---|---|---|---|---|
| 1 | Ph | H | H | $HOCH_2$ |
| 2 | Ph | $CH_3$ | H | $HOCH_2$ |
| 3 | Ph | $CH_3CH_2$ | H | $HOCH_2$ |
| 4 | Ph | $CH_3CH_2CH_2$ | H | $HOCH_2$ |
| 5 | Ph | $(CH_3)_2CH$ | H | $HOCH_2$ |
| 6 | Ph | $HOCH_2$ | H | $HOCH_2$ |
| 7 | Ph | $CH_3CHOH$ | H | $HOCH_2$ |
| 8 | Ph | $(CH_3)_2COH$ | H | $HOCH_2$ |
| 9 | Ph | $F-CH_2$ | H | $HOCH_2$ |
| 10 | Ph | $F_2CH$ | H | $HOCH_2$ |
| 11 | Ph | $F_3C$ | H | $HOCH_2$ |
| 12 | Ph | $CH_3CHF$ | H | $HOCH_2$ |
| 13 | Ph | $CH_3CF_2$ | H | $HOCH_2$ |
| 14 | Ph | $(CH_3)_2CF$ | H | $HOCH_2$ |
| 15 | Ph | $DMTBS-OCH_2$ | H | $HOCH_2$ |
| 16 | Ph | $DPTBS-OCH_2$ | H | $HOCH_2$ |
| 17 | Ph | $TPS-OCH_2$ | H | $HOCH_2$ |
| 18 | Ph | $IPDMS-OCH_2$ | H | $HOCH_2$ |
| 19 | Ph | $CH_3CH(O-DMTBS)$ | H | $HOCH_2$ |
| 20 | Ph | $CH_3CH(O-DPTBS)$ | H | $HOCH_2$ |
| 21 | $CH_3$ | $CH_3CH(O-TPS)$ | H | $HOCH_2$ |
| 22 | $CH_3$ | $CH_3CH(O-IPDMS)$ | H | $HOCH_2$ |
| 23 | $CH_3$ | $(CH_3)_2C(O-DMTBS)$ | H | $HOCH_2$ |
| 24 | $CH_3$ | $(CH_3)_2C(O-DPTBS)$ | H | $HOCH_2$ |
| 25 | $CH_3$ | $(CH_3)_2C(O-TPS)$ | H | $HOCH_2$ |
| 26 | $CH_3$ | $(CH_3)_2C(O-IPDMS)$ | H | $HOCH_2$ |
| 27 | $CH_3$ | H | H | $COOCH_3$ |
| 28 | $CH_3$ | $CH_3$ | H | $COOCH_3$ |
| 29 | $CH_3$ | $CH_3CH_2$ | H | $COOCH_3$ |
| 30 | $CH_3$ | $CH_3CH_2CH_2$ | H | $COOCH_3$ |
| 31 | $CH_3$ | $(CH_3)CH$ | H | $COOCH_3$ |
| 32 | $CH_3$ | $HOCH_2$ | H | $COOCH_3$ |
| 33 | $CH_3$ | $CH_3CHOH$ | H | $COOCH_3$ |
| 34 | $CH_3$ | $(CH_3)_2COH$ | H | $COOCH_3$ |
| 35 | $CH_3$ | $FCH_2$ | H | $COOCH_3$ |
| 36 | $CH_3$ | $F_2CH$ | H | $COOCH_3$ |
| 37 | $CH_3$ | $F_3C$ | H | $COOCH_3$ |
| 38 | $CH_3$ | $CH_3CHF$ | H | $COOCH_3$ |
| 39 | $CH_3$ | $CH_3CF_2$ | H | $COOCH_3$ |

-continued

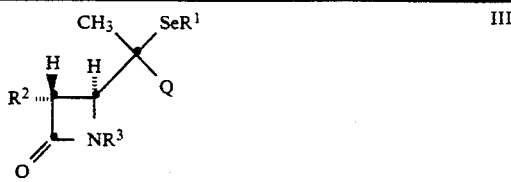

| Compound | R¹ | R² | R³ | Q |
|---|---|---|---|---|
| 40 | $CH_3$ | $(CH_3)_2CF$ | H | $COOCH_3$ |
| 41 | 4-Pyr | DMTBS—$OCH_2$ | H | $COOCH_3$ |
| 42 | 4-Pyr | DPTBS—$OCH_2$ | H | $COOCH_3$ |
| 43 | 4-Pyr | TPS—$OCH_2$ | H | $COOCH_3$ |
| 44 | 4-Pyr | IPDMS—$OCH_2$ | H | $COOCH_3$ |
| 45 | 4-Pyr | $CH_3CH(O-DMTBS)$ | H | $COOCH_3$ |
| 46 | 4-Pyr | $CH_3CH(O-DPTBS)$ | H | $COOCH_3$ |
| 47 | 4-Pyr | $CH_3CH(O-TPS)$ | H | $COOCH_3$ |
| 48 | 4-Pyr | $CH_3CH(O-IPDMS)$ | H | $COOCH_3$ |
| 49 | 4-Pyr | $(CH_3)_2C(O-DMTBS)$ | H | $COOCH_3$ |
| 50 | 4-Pyr | $(CH_3)_2C(O-TPS)$ | H | $COOCH_3$ |
| 51 | 4-Pyr | $(CH_3)_2C(O-IPDMS)$ | H | $COOCH_3$ |
| 52 | 4-Pyr | H | DMTBS | COOH |
| 53 | 4-Pyr | $CH_3$ | DMTBS | COOH |
| 54 | p-Tol | $CH_3CH_2$ | DMTBS | COOH |
| 55 | p-Tol | $CH_3CH_2CH_2$ | DPTBS | $COOCH_2CH_3$ |
| 56 | p-Tol | $(CH_3)_2CH$ | DPTBS | $COOCH_2CH_3$ |
| 57 | p-Tol | $HOCH_2$ | DPTBS | $COOCH_2CH_3$ |
| 58 | p-Tol | $CH_3CHOH$ | TPS | $COOCH_2CH_2CH_3$ |
| 59 | p-Tol | $(CH_3)_2COH$ | TPS | $COOCH_2CH_2CH_3$ |
| 60 | p-Tol | $FCH_2$ | TPS | $COOCH_2CH_2CH_3$ |
| 61 | p-Tol | $F_2CH$ | IPDMS | $COOCH(CH_3)_2$ |
| 62 | p-Tol | $F_3C$ | IPDMS | $COOCH(CH_3)_2$ |
| 63 | p-Tol | $CH_3CHF$ | IPDMS | $COOCH(CH_3)_2$ |
| 64 | p-Tol | $CH_3CF_2$ | H | $COO(CH_2)_3CH_3$ |
| 65 | p-Tol | $(CH_3)_2CF$ | H | $COO(CH_2)_3CH_3$ |
| 66 | p-MeOPh | DMTBS—$OCH_2$ | H | $COO(CH_2)_3CH_3$ |
| 67 | p-MeOPh | DPTBS—$OCH_2$ | H | $COOCH_2CH(CH_3)_2$ |
| 68 | p-MeOPh | TPS—$OCH_2$ | H | $COOCH_2CH(CH_3)_2$ |
| 69 | p-MeOPh | IPDMS—$OCH_2$ | H | $COOCH_2CH(CH_3)_2$ |
| 70 | p-MeOPh | $CH_3CH(O-DMTBS)$ | H | $COOCH(CH_3)CH_2CH_3$ |
| 71 | p-MeOPh | $CH_3CH(O-DPTBS)$ | H | $COOCH(CH_3)CH_2CH_3$ |
| 72 | p-MeOPh | $CH_3CH(O-TPS)$ | H | $COOCH(CH_3)CH_2CH_3$ |
| 73 | p-MeOPh | $CH_3CH(O-IPDMS)$ | H | $COOC(CH_3)_3$ |
| 74 | p-MeOPh | $(CH_3)_2C(O-DMTBS)$ | H | $COOC(CH_3)_3$ |
| 75 | p-MeOPh | $(CH_3)_2C(O-DPTBS)$ | H | $COOC(CH_3)_3$ |
| 76 | p-MeOPh | $(CH_3)_2C(O-TPS)$ | H | $COOC(CH_3)_3$ |
| 77 | p-MeOPh | $(CH_3)_2C(O-IPDMS)$ | H | $COOC(CH_3)_3$ |

The abbreviations for the silyl protecting groups DMTBS et al. are described hereinabove and for $R^1$ include Ph=phenyl, 4-Pyr=4-pyridyl, p-Tol=p-tolyl and p-MeOph=p-methoxyphenyl.

The structures and formulas representative of Structure IV given in the above Table are not intended to be limiting, and other combinations of $R^1$, $R^2$, $R^3$, Q and X and their resulting species of Structure IV, which will be obvious to one skilled in the art in light of this disclosure are also deemed to be included within the scope of this invention.

A preferred class of the compositions is of the structural formula:

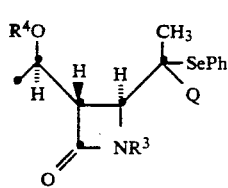

wherein $R^3$ and $R^4$ are independently hydrogen or a blocking group.

Particularly preferred are the compositions of the structural formula:

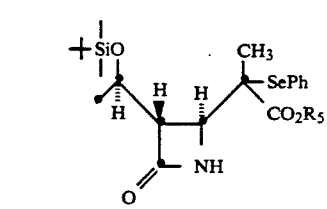

wherein $R^5$ is H or $C_1$-$C_4$ alkyl, preferably methyl.

A further preferred compound is

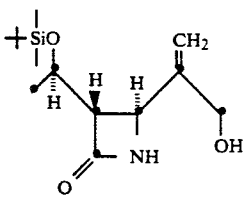

The following examples are illustrative of the best mode of carrying out the invention as contemplated by us and should not be construed to be limitations on the scope or spirit of the instant invention.

EXAMPLE 1

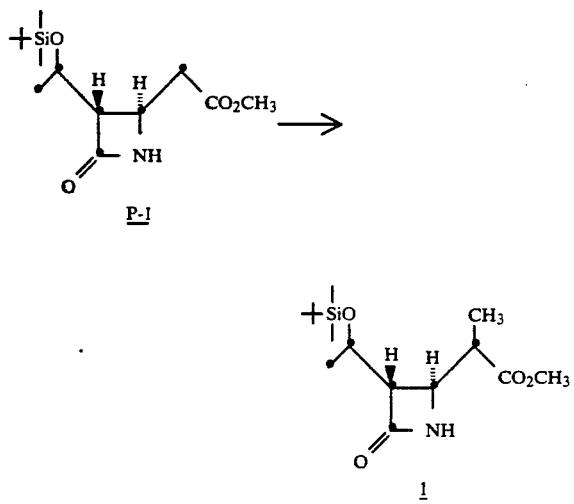

P-1

1

To 193.2 mg (0.640 mmol) of P-1 (prepared by the method of D. H. Shih et al., in *Heterocycles* 1984, Vol. 21, pp. 29–40, hereby incorporated by reference for this purpose) in 3 ml of anhydrous tetrahydrofuran (THF) at −78° C. was added 1.602 mmole of KN(SiMe$_3$)$_2$ in 2.44 ml anhydrous toluene dropwise with stirring over a period of 5 minutes under N$_2$. After the addition was complete, the temperature was raised to −50° C. The reaction mixture had a jelly-like consistency and 2 ml anhydrous THF was added to solubilize the contents. The mixture was then stirred at −50° C. (12° C.) for 1 hour then cooled back to −78° C. Then 0.10 ml (227.5 mg, 1.602 mmol) of methyl iodide (Aldrich) was added to the stirred mixture over a 25 minute period during which a precipitate was observed. The reaction mixture was stirred at −78° C. for one hour after complete addition of methyl iodide. At −78° C., 1.0 ml of saturated aqueous ammonium chloride was added. The organic layer was separated and the aqueous layer extracted with 2×10 ml CH$_2$Cl$_2$. The combined organic portions were dried over anhydrous potassium carbonate. Removal of the organic solvent in vacuo afforded 174.2 mg (86.3% of theory) of crude product. Analysis by liquid chromatography using a Altex Ultrasphere-Octyl, 5μ, 25 cm×4.6 mm I.D., column and eluting with acetonitrile: water:H$_3$PO$_4$, 60:40:0.1, solvent system showed a weight ratio of alpha/beta epimers of 12.4.

Proton NMR (250 MHz) verified the chromatography results.

EXAMPLE 2

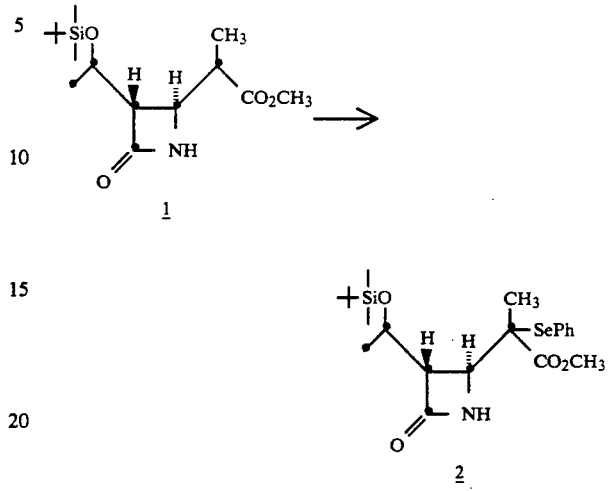

1

2

At −40° C. under nitrogen, 1.84M n-butyl-lithium in hexane (70 ml, 128.25 mmol) was added to a stirred solution of diisopropylamine (21.6 ml, 153.9 mmol) in anhydrous tetrahydrofuran (80 ml). The temperature was kept below −10° C. (15 minutes). At −50° C., 1 from Example 1 (16.2 g, 51.3 mmol ) was added as a solid via sidearm, and tetrahydrofuran (40 ml) were added to aid dissolution, and the reaction mixture held at 40 at 45° C. for about 3.5 hours. A solution of phenylselenenylchoride (24.6, 128.25 mmol) in tetrahydrofuran (40 ml) were added at −70° to −75° C. dropwise under N$_2$ pressure over 25 minutes. After stirring for 15–20 minutes at −78° C., 0.5N HCl (150 ml) were added and the reaction contents allowed to warm to room temperature. Then was added 100 ml. more of 0.5N HCl and the reaction mixture poured into a separatory funnel with Et$_2$O (200 ml). The organic layer was separated, and the aqueous layer was again extracted with Et$_2$O (100 ml). The combined ether layers were washed with brine (100 ml), dried over Na$_2$SO$_4$, filtered and concentrated in vacuo to give crude 2. The crude was treated with hexane at room temperature to yield 8.7 g of a single diastereoisomer, the beta-methyl form as shown by proton NMR (CDCl$_3$). The hexane filtrate was concentrated and treated by chromatography on Baker's silica gel (170 g), gradually eluting with hexane, then 1:9 ethyl acetate/hexane, then 1:1 ethyl acetate in hexane, providing a mixture of the beta and alpha diastereomers (14.5 g, 60% yield), in a 55/45 alpha/beta weight ratio as determined by proton NMR. Total weight of product was 23.2 g (96%, 24.14 g).

The reported nuclear magnetic resonance (NMR) values herein were obtained at 250 or 300 MHz in deuterochloroform solvent, using tetramethylsilane as the internal standard. The values are reported in dimensionless delta ( ) units. Abbreviations used include s=singlet, d=doublet, m=multiplet, br. s.=broad singlet. Coupling constants are reported as J.

Infrared (IR) spectroscopic absorption frequencies taken in methylene chloride solvent are reported for specific functional groups in cm$^{-1}$.

Mass spectrum (ms) data is also presented showing the most abundant mass/charge peak in the spectrum corresponding to the molecular ion (MI) being the molecular weight of the parent, or the trimethylsilyl (TMS) derivative.

Melting points (mp) are presented together with solvent(s) used for recrystallization.

Data for Major Diastereomer 2: NMR (CDCl₃, TMS): δ. 0.04 & 0.08 [2 singlets, Si(CH₃)₂]. 0.86 [s, SiC(CH₃)₃]. 1.31 (d, CH₃CHOSi). 1.53 (s, CH₃CSe). 3.06 (m, H₃). 3.62 (s, OCH₃). 4.22 (d, J=2 Hz, H₄). 4.26 (m, CHOSi). 5.80 (br.s., NH). 7.30–7.69 (aromatic protons).

IR (CH₂Cl₂)3400 (NH), 1769 (β-lactam C=O), 1725 (ester C=O) cm⁻¹. mp (recrd. hexane), 115°–118° C.

Data for Minor Diastereomer 2: NMR (CDCl₃, TMS): δ. 0.07 [s, Si(CH₃)₂]. 0.87 [s, SiC(CH₃)₃]. 1.22 (d, CH₃CHOSi). 1.48 (s, CH₃CSe). 3.18 (m, H₃). 3.68 (s, OCH₃). 4.00 (d, J=2 Hz, H₄). 4.27 (m, CH₃CHOSi). 6.05 (br.s, NH). 7.32–7.67 (aromatic protons).

IR (CH₂Cl₂)3400 (NH), 1769 (β-lactam C=O), 1725 (ester C=O) cm⁻¹.

mp (recrd. hexane), 128°–130° C.

EXAMPLE 3

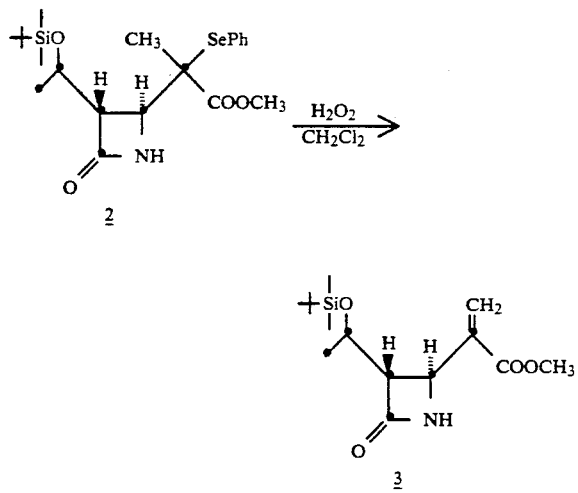

To five hundred (500) mg of 2, prepared in Example 2, dissolved in 15 ml, methylene chloride at room temperature (RT) was added dropwise with stirring 1 ml of 30% aqueous hydrogen peroxide. The reaction proceeded instantly as indicated by the color changes from a yellow to colorless. After the addition was complete, the reaction mixture was allowed to stir at RT for 30 minutes. Ten ml of water were added, followed by 10 ml methylene chloride and the layers were separated. The organic layer was washed with 2×10 ml 5% NaHCO₃ solution and the 1×10 ml, saturated NaCl solution and then dried over anhydrous sodium sulfate. The organic solvent was evaporated in vacuo to yield 320 mg (96.1% of theory) of 3. Analysis for 3 included:

Anal. Calcd. for C₁₅H₂₇NO₄Si: C, 57.46; H, 8.70; N, 4.47.

Found: C, 57.51; H, 8.54; N, 4.49.

'H-NMR (CDCl₃, TMS)δ. 6.49 (Broad s, NH).

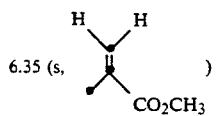

6.35 (s, CO₂CH₃)

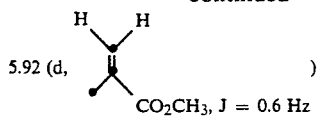

5.92 (d, CO₂CH₃, J = 0.6 Hz)

4.58 (broad s, C4-H). 4.27 (q of d, CH₃CHOS:, J=6.3, 3.6 Hz). 3.80 (s, OCH₃). 3.00 (broad s, C3-H). 1.29 (d, CH₃CHOS:, J=6.3 Hz). 0.88 (s, tBuSiMe₂). 0 07, 0.06 (s, tBuSiMe₂).

HPLC Assay: Altex silica gel, 5M, 25 cm×4.6 mm ID, isopropanol:hexanes, 4:96, v/v/1.1 ml 1 minute, 210 nm, sample injection volume: 10 μl, sample concentration:1 mg/component/ml. Retention times (minute):

| 1, | (β-Me-COOMe, 6.40 |
| | α-Me-COOMe, 8.00 |
| 2, | 3.83 |
| 3, | 4.89 |

EXAMPLE 3A

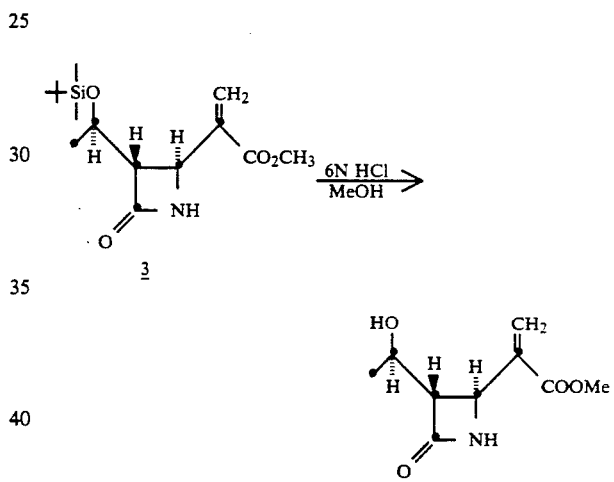

In 65 ml of MeOH 3 crude mixture (5.7036 g) was treated with 7.0 ml of 6NHCl. After stirring at room temperature for 3 hours, 15 ml of 0.1N Na₂HPO₄ was added followed by 50 ml of 10% NaHCO₃. The crude mixture was concentrated in vacuo to half volume and diluted with ethyl acetate. The organic phase was extracted and the aqueous back extracted (3×20 ml) with EtOAc. The combined organic layers were dried over anhydrous MgSO₄. The filtrate was concentrated in vacuo to afford 3.1977 g (83.8%) of crude material. The crude material was recrystallized from ether to obtained 1.0637 g (38%).

Anal. Calcd. for C₉H₁₂NO₄: C, 54.53; H, 6.11; N, 7.07.

Found: C, 54.16; H, 6.76; N, 6.83.

'HNMR (CDCl₂, TMS)δ.

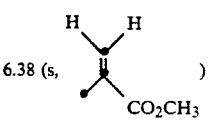

6.38 (s, CO₂CH₃)

6.35 (broad s, NH).

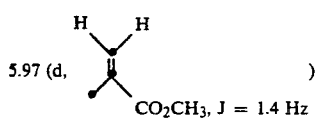

5.97 (d, $CO_2CH_3$, J = 1.4 Hz)

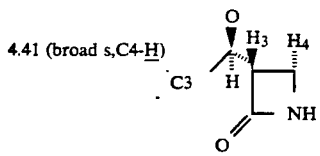

4.41 (broad s, C4-H)

4.21 (q of d, $CH_3CHOH$, J=8.5, 2.2 Hz). 3.83 (s, —$OCH_3$). 2.93 (dd, C2-H, J=8.5, 2.2 Hz). 1.36 (d, $CH_3CHOH$, J=6.3 Hz).

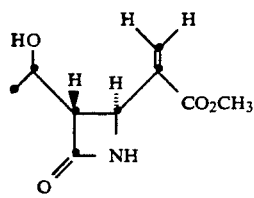

13-NMR ($CDCL_3$, TMS)δ. 167.5 (s, C=O). 166.3 (s, C-O). 138.7 (s, —C=$CH_2$). 124.8 (t, —C=$CH_2$). 66.1, 65.8 (d, $CH_2CHOH$, C-3). 51.9 (C-4). 51.3 (q, $OCH_3$). 20.6 (q, $CH_3CHOH$).

EXAMPLE 4

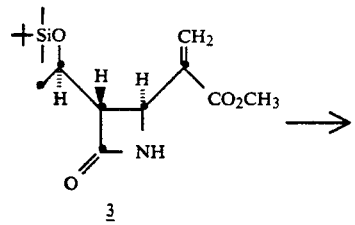

3

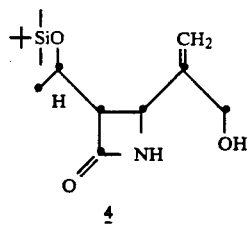

4

At −78° C., 2.8 ml of a solution of diisobutyl aluminum hydride (DIBAL, 4.25 mmol) in anhydrous toluene was added via syringe under moisture exclusion conditions to 3 (from Example 3, 320 mg, 1.02 mmol, in 5 ml anhydrous THG. The reaction was followed by liquid chromatography to show presence of intermediate aldehyde and final alcohol reduction product.

The cooling bath was removed and the contents stirred at RT for one hour and then 2.0 ml additional DIBAL added and stirred for 1 hour. TLC showed complete conversion of aldehyde to alcohol. Isopropanol (1.0 ml) was then added at 0°-5° C., followed by 0.5 NHCl to give an aqueous pH 3.5–4.0, and ethyl acetate added to smooth the resulting gelatinous mass. Filter cel and water were added and the contents filtered and the filter cake washed with ethyl acetate. The organic layers were combined, washed with sodium bicarbonate solution, saturated sodium chloride solution, then dried over anhydrous sodium sulfate. The organic solvent was evaporated in vacuo to yield 250 mg (86% of theory of 4.

Anal. Calcd. for $C_{14}H_{27}NO_3Si$: C, 58.89; H, 9.55; N, 4.91.

Found: C, 58.85; H, 9.23; N, 4.86.

13C ($CDCl_3$)δ. 169.0 (C=O). 147.2 (—C=$CH_2$). 111.3 (—C—$CH_2$. 66.1, 65.3, 63.3 ($CH_3CHOH$, C-3, C-4). 52.4 ($OCH_3$). 25.7 ($CCH_3)_3SiMe_2$). 22.5 ($CH_3CHOH$). 17.89 (—$CH_2OH$). −4.4, −4.8 (+$SiMe_2$).

EXAMPLE 5

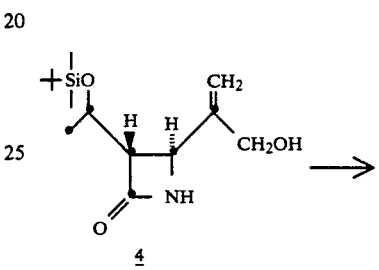

4

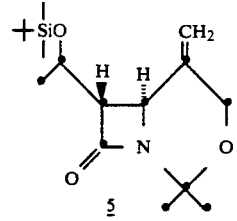

5

To a solution of 4 (215.6 mg, 0.754 mmol from Example 4) in sieve-dried methylene chloride (6.0 ml) was added 2,2-dimethoxypropane (108 microl., 0.875 mmol) and $BF_3.Et_2O$-(28 microl.). After stirring at room temperature under nitrogen for 30 minutes, 50 microliters of triethylamine were added to complex the boron trifluoride. The reaction mixture was filtered through a 1 cm silica gel (E. Merck 60 250–400 mesh) eluting with methylene chloride (20 ml). The solution was concentrated in vacuo to yield 231.9 mg, (94.7%) of 5. Data for Product of Step E:

NMR ($CDCl_3$, TMS)δ. 0.07 & 0.08 [2 singlets, Si($CH_3)_2$]. 0.88 [s, SiC($CH_3)_3$]. 1.25 (d, $CH_3CHOSi$). 1.44 & 1.71 [2 singlets, ($CH_3)_2C$]. 3.04 (dd, J=2 & 4Hz, $H_7$). 4.16–4.34 (m, $H_6$, $CH_3CHOSi$, & $CH_2O$). 4.96 & 5.08 (2 br S, $CH_2$=C).

IR ($CH_2Cl_2$) 1750 (β-Lactam C=O) $cm^{-1}$. mp 46°-48° C.

M.S. 268 (MI-t-butyl), 166 (MI-$CH_3CHOtBDMSi$).

Anal. Calcd. for $C_{17}H_{33}NO_3Si$: C, 62.32; H, 10.07; N, 4.20.

Found: C, 62.31; H, 9.52; N, 4.01.

EXAMPLE 6

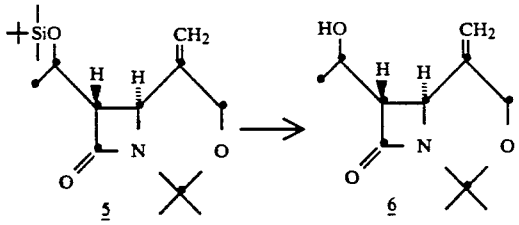

To a solution of 5 (6.98 g, 21.53 mmol) in 70 ml anhydrous dimethylformamide at 0° C. under nitrogen was added 1M tetrabutylammonium fluoride in tetrahydrofuran (23.7 ml, 23.7 mmole), over 10 minutes and stirring was continued for 3 hours under nitrogen at room temperature. The DMF was removed in vacuo to leave a residue which was treated with 150 ml diethylether and 100 ml of saturated ammonium chloride solution. The aqueous layer was separated and extracted with 100 ml diethyl ether. The combined ether layers were washed two times with brine, dried, filtered and concentrated in vacuo to give crude 6, 4.1 g (theory 4.5 g). Chromatography on a small column of Baker's silica gel, eluting with 0% to 50% ethyl acetate in methylene chloride, ($R_f$=0.5) provided purified 6 (3.30 g, 73% yield). Data for Product 6:

NMR (CDCl$_3$, TMS); δ. 1.33 (d, J=6Hz, CH$_3$CHOH). 1.47 & 1.73 (2 singlets, (CH$_3$)$_2$C). 2.62 (br, OH). 3.08 (dd, J=2 & 5Hz, H$_7$). 4.22 (m, H$_6$, CH$_3$CHOH, & CH$_2$O). 5.05 (center of m, CH$_2$=C).

IR (CH$_2$Cl$_2$) 3650 (OH), 1746 (C=O) cm$^{-1}$.

Anal. Calcd. for C$_{11}$H$_{17}$NO$_3$: C, 62.52; H, 8.13; N, 6.63.

Found: C, 60.90; H, 8.13; N, 6.17.

EXAMPLE 7

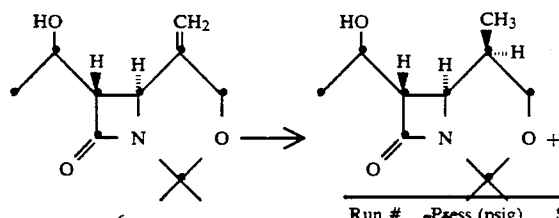

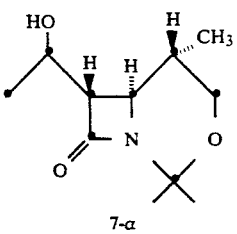

Raney Nickel, commercially obtained from W. R. Grace Co., as Grace No. 28 Type Raney Nickel (W-4), was washed repeatedly with ethyl acetate, then with MeOH. At 0° C., with magnetic stirring, 0.32 g of the washed catalyst (109 wt. %) was added with 0.30 g (1.51 mmoles) of 6 in 20 ml of MeOH under atmospheric pressure of H$_2$ for 4 hours, and the reaction mixture shaken on a Parr apparatus at room temperature under 40 psig H$_2$ for 2.5 hours. The reaction mixture was then filtered through Celite, rinsing with MeOH. The filtrate was concentrated in vacuo to afford 7-β/α in a quantitative yield. The product isolated contains a mixture of 7-β and 7α in a molar ratio of 95:5 as approximated by 250 MHz NMR analysis and HPLC. Data for Products 7:

NMR (CDCl$_3$, TMS); δ. 0.91 (d, α-CH$_3$). 1 12 (d, β-CH$_3$). 1.30 (d, CH$_3$CHOH of 7β). 1.31 (d, CH$_3$CHOH of 7α). 1.42 & 1.74 (2 singlets, (CH$_3$)$_2$C of 7β). 1.41 & 1.75 (2 singlets, (CH$_3$)$_2$C of 7α). 1.87 (d, OH). 1.96 (m, H$_5$). 2.83 (dd, J=2 & 5.5 Hz, H$_7$ of 7α). 3.06 (dd, J=2 & 6 Hz, H$_7$ of 7β). 3.18 (dd, J=2 & 10 Hz, H$_6$ of 7α). 3.46 (t, J$_{4,4}$=J$_{4,5}$=12 Hz, H$_4$ of 7α). 3.60 (dd, J$_{4,4}$=12 Hz, J$_{4,5}$=3 Hz, H$_4$ of 7β). 3.73 (dd, J$_{4,4}$=12 Hz, J$_{4,5}$=4.5 Hz, H$_4$ of 7α). 3.80 (dd, J=2 & 5 Hz, H$_6$ of 7β). 3.98 (dd, J$_{4,4}$=12 Hz, J$_{4,5}$=2 Hz, H$_4$ of 7β). 4.16 (m, CH$_3$CHOH).

MS (of TMS derivative) 285 (MI), 270 (MI-CH$_3$).

Anal. Calcd. for C$_{11}$H$_{19}$NO$_3$: C, 62.52; H, 8.13; N, 6.63.

Found: C, 60.90; H, 8.14; N, 6.17.

Additional runs were made for comparison purposes in which the catalyst, solvent, pressure, temperature, catalyst loading and reduction time were varied. The results are listed below in Table I.

TABLE I

| Run # | Press (psig) | Solvent | Temp. | Catalyst | β/α | Time (hr.) |
|---|---|---|---|---|---|---|
| 1 | 40 | DMSO | r.t. | 1,1'Cp$_2$Fe(φ$_2$P)$_2$PdCl$_2$[g] | NR | 24 |
| 2 | 40 | EtOH | " | Ni$_2$B | " | 22 |
| 3 | 40 | MeOH | " | 5% Rh/Al$_2$O$_3$ | 84.8/15.2 | 6 |
| 4 | 1380 | " | −40 + r.t. | 5% Ru/C | 49.7/50.3[a] | 22 |
| 5 | 40 | " | r.t. | RaNi((+) tartaric acid)[b] | 93.8/6.2 | 9 |
| 6 | 40 | EtOH | " | RaNi(EtOH)[c] | 90.5/9.5 | 5 |
| 7 | 40 | EtOAc | " | RaNi(EtOAc)[d] | 78.6/21.4 | 4 |
| 8 | 40 | EtOH | " | RaNi(EtOAc) | 91.7/8.3 | 4 |
| 9 | 40 | MeOH | " | " | 91.5/8.5 | 4 |
| 10 | 2 | EtOH | " | " | 92.8/7.2 | 5 |
| 11 | atmospheric[e] | MeOH | 0° | " | 89.8/10.2 | 15 |
| 12 | atmospheric[f] | " | " | " | 94.5/5.1 | 4 |

[a]12.1% of starting material remaining.
[b]Raney nickel marinated with (+)-tartaric acid at r.t. in EtOH.
[c]Raney nickel washed with EtOH only.
[d]Raney nickel washed with EtOH then EtOAc.
[e]Magnetic stirring with 16 wt % catalyst loading.
[f]Magnetic stirring with 109 wt % catalyst loading.
[g]Cp = cyclopentadienyl In order to enhance the hydrogen bonding between the hydroxyl group and the carbonyl group, which we theorized should increase the three dimensional structural rigidity of the molecule and thus provide a more selective absorption on the catalyst, the reduction was carried out in ethyl acetate with Raney nickel washed and aged in ethyl acetate for several days. Surprisingly, the β/α ratio dropped to 78.6/21.4 (Run 7). The use of ethyl acetate washed Raney nickel, designated as RaNi(EtOAc), in ethanol gave a slightly better selectivity (Run 8), a 91.7% of the β was obtained with respect to the 90.5% observed earlier. This result indicated that the hydrogen bonding may be detrimental to selectivity and by disrupting this hydrogen bonding by the use of the hydroxylic solvent the hydroxyl group is then available for participating in absorption process on the catalyst which ultimately provides a better β/α ratio. Switching the solvent to methanol (Run 9) gave essentially the same result as in ethanol. When the hydrogen pressure is decreased to 2 psig (Run 10), the selectivity again went up slightly giving 92.8% β-isomer. Subsequently the reductions are carried out at atmospheric pressure. At 16 wt% catalyst loading and 0° C. (Run 11), the reduction was complete in 15 hours giving 89.8% of the β-isomer. Increasing the catalyst loading to 109% gave a high of 94.9% of the β-isomer in 4 hours. Since Raney nickel catalyst is paramagnetic and sticks to magnetic stir bars rendering most of the surface area of the catalyst charged not available for reduction, and because the mixing method used in the atmospheric reduction runs was with magnetic stirring, the actual catalyst loading required to obtain the 95/5 ratio should be less than the 109% charged. Raney nickel that has been marinated with (+)-tartaric acid in ethanol gave excellent selectivity even at room temperature and 40 psig (Run 5). Other catalysts that were tried are: 1,1'-bisdiphenylphosphinoferrocenylpalladium chloride (Run 1); nickel boride (Run 2); 5% Rh/Al₂O₃ (Run 3); and 5% Ru/C (Run 4), which gave all inferior results.

EXAMPLE 8

"One-Pot" Reaction

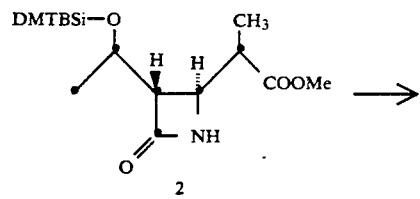

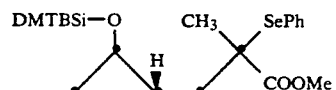

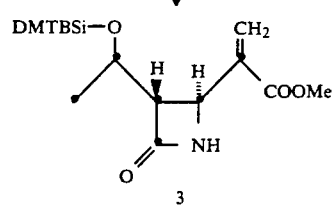

Procedure:

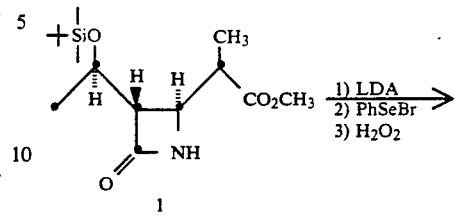

The enolate was generated following Example 2 procedure using 17.208 mmole of 1. The oxidation was carried on the crude material following Example 3 to afford 5.7036 (95.9%) isolated yield of 3.

EXAMPLE 9

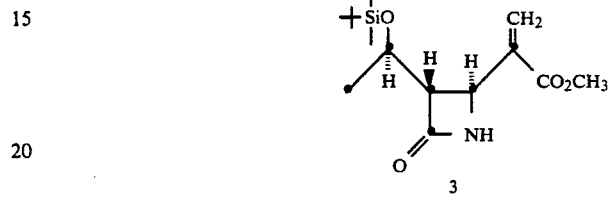

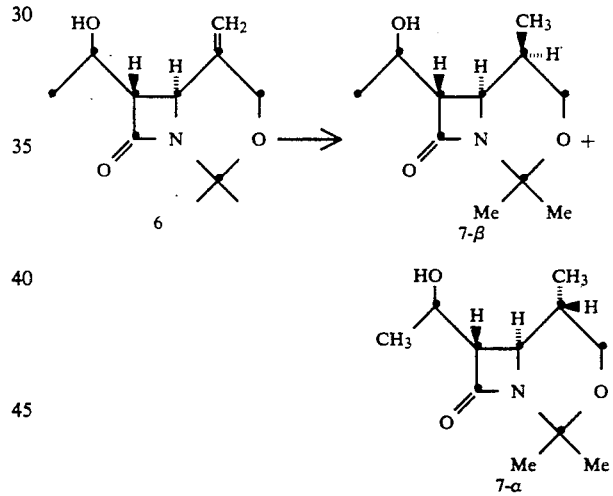

Procedure

Following Example 7, 1.14 g (5.4 mmoles) of 6 was hydrogenated to 7β/7α (94.6:5.4) in a quantitative yield. The crude reaction mixture was treated with 1.0 g (6.63 mmole) of t-butyldimethylsilychloride and 1.5 ml of triethylamine in 10 ml of DMF. The reaction mixture was stirred at room temperature for 6 hours. At 0° C., 50 ml of CH₂Cl₂ were added followed by 25 ml 1N HCl. The CH₂Cl₂ layer was extracted and washed with 25 ml H₂O, 25 ml NaHCO₃, 25 ml H₂O. The combined organic layer was dried over MgSO₄ and concentrated "in vacuo" to afford 1.83 g of crude material. The product was purified by flash chromatography using 20% ethyl acetate:hexanes (R$_f$=0.20) to afford 1.4502 g (82.4%) isolated yield.

¹H NMR (CDCl₃, CHCl₃)δ. 0.08, 0.07, s, 6H, SiMe₂. 0.88, s, 9H, tBuSi. 1.11, d, 3H, β-CH₃. J=7.05 Hz. 1.18, d, 3H, CH₃CHOSi, J=6.23 Hz. 1.72, 1.40, s, 6H, (CH3)2C. 1.89, m, 1H, H5. 2.98, dd, 1H, H3, J=4.27, 1.98 Hz. 3.58, dd, 1H, H6, J=12.06, 3.04 Hz. 3.82, dd, 1H, H4, J=5.08, 1.95 Hz. 3.96, dd, 1H, H6, J=12.05, 2.44 Hz. 4.17, qd, 1H, CH3CHOSi, J=6.23, 1.94 Hz.

Anal. Calcd. for C17H33NO3Si: C, 62.32; H, 10.17; N, 4.28.

Found: C, 62.31; H, 9.52; N, 4.01.

Procedure

EXAMPLE 10

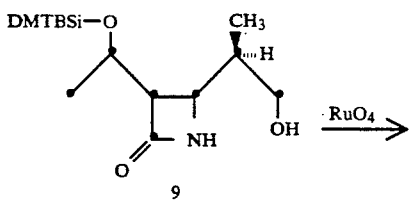

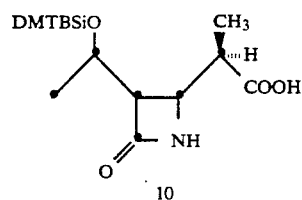

Into a 50 ml flask containing a biphasic mixture of 2 ml CCl4, 2 ml CH3CN, 3 ml H2O, 212.5 mg of 9 (prepared as in Example 4 from 1-β) and 876.4 mg NaIO4, were added 7.3 mg of RuCl3.H2O. The resulting mixture was stirred vigorously for 15 minutes at room temperature and then 10 ml CH2Cl2 was added resulting in phase separation. The upper aqueous layer was extracted with 3×15 ml CH2Cl2, organic portions were combined, and dried over MgSO4 and concentrated in vacuo to a residue. The residue was diluted with 20 ml of diethyl ether, filtered through Celite and the ether evaporated to yield 217.3 mg (97.5% of theory) of the beta-acid 10. Analysis of 10 showed:

EXAMPLE 11

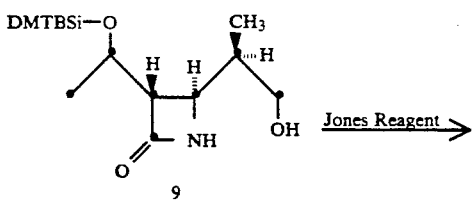

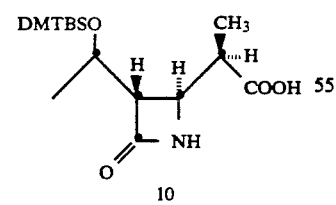

Into a 10 ml flask containing 119.0 mg (0.413 mmol) of 9 (prepared in Example 4 from 1-β) in 5 ml diethyl ether at 0° C., was added Jones Reagent (prepared from 67 g. CrO3, 125 and H2O, 58 ml H2SO4, 10 ml H2O, as per the procedure in Organic Synthesis, Vol. V, p. 310) by titration until a permanent orange color was present. Ten ml of CH2Cl2 and 10 ml of H2O were added with stirring and the layers separated, the aqueous layer was extracted with 3×10 ml methylene chloride, organic portions combined, and dried over MgSO4, filtered through silica gel (E. Merck, 230–400 micron mesh) to yield 125.2 mg (90.7% of theory) of beta-acid 10 that crystallized upon standing into crystals. Analysis of 10 showed:

HPLC Assay: Altex Ultrasphere-Octyl, 5μ, 25 cm×4.6 mm ID, acetonitrile: water: H3PO4, 55:40:0.1, v/v/ 1.1 ml/min, 210 nm, sample injection volume: 10 μl, sample concentration: 1 mg/component/ml. Retention times (min): α-Me-COOH, 7.31; α-Me-COOH, 8.45.

1H-NMR (250 MHz, CDCl3)δ. 6.26 (broad s, 1H, NH). 4.19 (q of d, 1H, J=6.2 Hz, J=4.5 Hz, C7-H). 3.93 (d of d, 1H, J-5,0 Hz, J=2.2 Hz, C4-H). 3.01 (d of d, 1H, J=4.3 Hz, J=2.2 Hz, C3-H). 2.73 (q of d, 1H, J=7.0 Hz, J=5.0 Hz, C5-H). 1.26 (d, 3H, J=7.0 Hz, C5-CH3) 1.18 (d, 3H, J=6.2 Hz, C8-H). 0.86 (s, 9H, tBuMe2Si). 0.06, 0.05 (s, 6H tBuMe2Si).

EXAMPLE 12

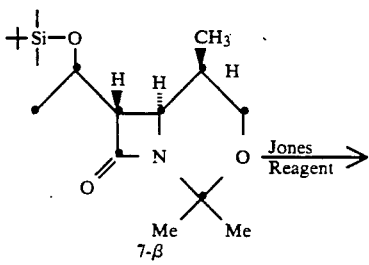

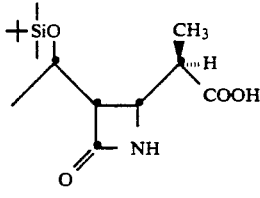

Procedure

Into a 25 ml flask containing 500 mg (1.527 mmole) of 7-β (prepared in Example 9) in 15 ml of acetone at 0° C., was added Jones Reagent (described in Example 11) by titration until a permanent orange color was present. Ten ml of CH2Cl2 and 10 ml of H2O were added with stirring and the layers separated, the aqueous was extracted with 3×10 ml CH2Cl2, organic portions combined, and dried over MgSO4, filtered through silica gel (E. Merck, 230–400 micron mesh) to yield 439.1 mg (95.4% of theory) of beta-acid 10 that crystallized upon standing into crystals.

Anal. Calcd. for C14H27SiNO4. C, 55.77; H, 9.04; N, 4.65.

Found: C, 55.95; H, 8.64; N, 4.29.

For 1H-NMR see Example 10.

What is claimed is:

1. A compound of the structural formula:

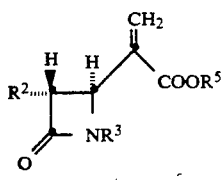

wherein $R^2$ is independently selected from hydrogen, linear or branched $C_1$–$C_3$ alkyl, which can be substituted with fluoro, hydroxy or protected hydroxy; $R^3$ is H or a protecting group and $R^5$ is hydrogen or $C_1$–$C_4$ alkyl.

2. The compound of claim 1 wherein said $R^2$ is independently selected from H, $CH_3$—, $CH_3CH_2$—, $(CH_3)_2CH$—, $HOCH_2$—, $CH_3CHOH$—, $CH_3CH_2CHOH$—, $(CH_3)_2COH$—, $FCH_2CHOH$—, $FCH_2$—, $F_2CH$—, $F_3C$—, $CH_3CHF$—, $CH_3CF_2$—, $(CH_3)_2CF$— or where said —OH is protected by trialkylsilyl, dialkylmonoarylsilyl, alkydiarylsilyl or triarylsilyl.

3. The compound of claim 2 wherein said $R^2$ is $(2R)CH_3CHOH$—.

4. The compound of claim 2 wherein said $R^2$ is $(2R)CH_3CH$— (dimethyl-t-butylsilyloxy).

5. The compound of claim 1 of the structural formula:

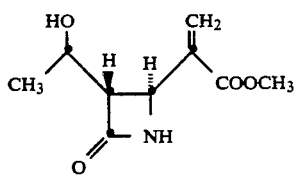

* * * * *